US008554524B2

(12) United States Patent
Saito et al.

(10) Patent No.: US 8,554,524 B2
(45) Date of Patent: Oct. 8, 2013

(54) CALCULATION METHOD FOR PHYSICAL VALUE, NUMERICAL ANALYSIS METHOD, CALCULATION PROGRAM FOR PHYSICAL VALUE, NUMERICAL ANALYSIS PROGRAM, CALCULATION DEVICE FOR PHYSICAL VALUE, AND NUMERICAL ANALYSIS DEVICE

(75) Inventors: Tsunehiro Saito, Tokyo (JP); Ken Uemura, Tokyo (JP); Satoshi Yoshida, Tokyo (JP); Shigeki Takano, Tokyo (JP); Yoshiichi Ozeki, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/336,575

(22) Filed: Dec. 23, 2011

(65) Prior Publication Data
US 2012/0095738 A1     Apr. 19, 2012

Related U.S. Application Data

(63) Continuation of application No. PCT/JP2010/060498, filed on Jun. 21, 2010.

(30) Foreign Application Priority Data

Jun. 25, 2009   (JP) ................................ 2009-150945

(51) Int. Cl.
     *G06F 17/10*      (2006.01)
(52) U.S. Cl.
     USPC ............................................................ 703/2
(58) Field of Classification Search
     USPC .......................................................... 703/2
     See application file for complete search history.

(56) References Cited

U.S. PATENT DOCUMENTS

| 5,129,035 | A | * | 7/1992 | Saji et al. ...................... 717/106 |
| 5,148,379 | A | * | 9/1992 | Konno et al. ...................... 703/2 |
| 5,408,638 | A | * | 4/1995 | Sagawa et al. ..................... 703/2 |
| 2008/0021684 | A1 | | 1/2008 | Dulac et al. |

OTHER PUBLICATIONS

Internation Search Report issued Sep. 14, 2010 in connection with International Application No. PCT/JP2010/060498, filed Jun. 21, 2010.

H. Noguchi "Meshfree/Ryushiho", Journal of the Japan Society of Simulation Technology, vol. 24, No. 4, pp. 34-42, (with English abstract). (Dec. 15, 2004).

(Continued)

*Primary Examiner* — Kamini S Shah
*Assistant Examiner* — Andre Pierre Louis
(74) *Attorney, Agent, or Firm* — Oblon, Spivak, McClelland, Maier & Neustadt, L.L.P.

(57) ABSTRACT

A calculation method for physical value for calculating physical values in a numerical analysis method for numerically analyzing a physical phenomenon, comprises a physical value calculation step of calculating physical values in an analysis domain divided into a plurality of divided domains, wherein in the physical value calculation step, the physical values are calculated by using: a discretized governing equation that uses values not requiring coordinates (Vertex) of vertices of the divided domains and connectivity information (Connectivity) of the vertices and that is derived on the basis of a weighted residual method; and a calculation data model in which volumes of the divided domains and characteristic values of boundary surface indicating characteristics of boundary surfaces of adjacent ones of the divided domains are provided as the values not requiring coordinates (Vertex) of vertices of the divided domains and connectivity information (Connectivity) of the vertices.

30 Claims, 24 Drawing Sheets

| | PRESENT INVENTION | FINITE ELEMENT METHOD AND FINITE VOLUME METHOD |
|---|---|---|
| PRE PROCESS | -CALCULATION DATA MODEL : NOT REQUIRING VERTEX AND CONNECTIVITY -ANALYSIS DOMAIN : INCLUDING DIVIDED DOMAINS OTHER THAN ORTHOGONAL GRID SHAPE | -CALCULATION DATA MODEL : REQUIRING VERTEX AND CONNECTIVITY -ANALYSIS DOMAIN : INCLUDING DIVIDED DOMAINS OTHER THAN ORTHOGONAL GRID SHAPE |
| SOLVER PROCESS | -PHYSICAL VALUE CALCULATION : NOT REQUIRING VERTEX AND CONNECTIVITY | -PHYSICAL VALUE CALCULATION : REQUIRING VERTEX AND CONNECTIVITY |

| | VOXEL METHOD | VOXEL METHOD (BOUNDARY CORRECTION) | PARTICLE METHOD |
|---|---|---|---|
| PRE PROCESS | -CALCULATION DATA MODEL : NOT REQUIRING VERTEX AND CONNECTIVITY -ANALYSIS DOMAIN : DIVIDED DOMAINS HAVE ONLY ORTHOGONAL GRID SHAPE | -CALCULATION DATA MODEL : REQUIRING VERTEX AND CONNECTIVITY -ANALYSIS DOMAIN : INCLUDING DIVIDED DOMAINS OTHER THAN ORTHOGONAL GRID SHAPE | -CALCULATION DATA MODEL : NOT REQUIRING VERTEX AND CONNECTIVITY : REQUIRING POSITIONS OF PARTICLES AND LINKAGE RELATION BETWEEN PARTICLES -ANALYSIS DOMAIN : DIVIDED DOMAINS ARE ABSENT |
| SOLVER PROCESS | -PHYSICAL VALUE CALCULATION : NOT REQUIRING VERTEX AND CONNECTIVITY | -PHYSICAL VALUE CALCULATION : REQUIRING VERTEX AND CONNECTIVITY | -PHYSICAL VALUE CALCULATION : NOT REQUIRING VERTEX AND CONNECTIVITY : REQUIRING TIME-DEPENDENT NEAR-NEIGHBOR ALGORITHMS |

(56) References Cited

OTHER PUBLICATIONS

Extended European Search Report Issued Oct. 24, 2012 in Patent Application No. 10792076.1.

B. van Hal et al., "Hybrid finite element—wave-based method for steady-state interior structural-acoustic problems", Computers and Structures, vol. 83, No. 2-3, XP027636960, 2005, pp. 167-180.

Eduardo Divo et al., "A meshless method for conjugate heat transfer problems", Engineering Analysis with Boundary Elements, vol. 29, No. 2, XP 027619027, 2005, pp. 136-149.

C.R. Schneidesch et al., "Chebyshev Collocation Method and Multi-domain Decomposition for Navier-Stokes Equations in Complex Curved Geometries", Journal of Computational Physics, vol. 106, No. 2, XP025759284, 1993, pp. 234-257.

U.S. Appl. No. 13/774,557, filed Feb. 22, 2013, Uemura, et al.

\* cited by examiner

FIG. 3

| | PRESENT INVENTION | FINITE ELEMENT METHOD AND FINITE VOLUME METHOD |
|---|---|---|
| PRE PROCESS | -CALCULATION DATA MODEL : NOT REQUIRING VERTEX AND CONNECTIVITY -ANALYSIS DOMAIN : INCLUDING DIVIDED DOMAINS OTHER THAN ORTHOGONAL GRID SHAPE | -CALCULATION DATA MODEL : REQUIRING VERTEX AND CONNECTIVITY -ANALYSIS DOMAIN : INCLUDING DIVIDED DOMAINS OTHER THAN ORTHOGONAL GRID SHAPE |
| SOLVER PROCESS | -PHYSICAL VALUE CALCULATION : NOT REQUIRING VERTEX AND CONNECTIVITY | -PHYSICAL VALUE CALCULATION : REQUIRING VERTEX AND CONNECTIVITY |

| | VOXEL METHOD | VOXEL METHOD (BOUNDARY CORRECTION) | PARTICLE METHOD |
|---|---|---|---|
| PRE PROCESS | -CALCULATION DATA MODEL : NOT REQUIRING VERTEX AND CONNECTIVITY -ANALYSIS DOMAIN : DIVIDED DOMAINS HAVE ONLY ORTHOGONAL GRID SHAPE | -CALCULATION DATA MODEL : REQUIRING VERTEX AND CONNECTIVITY -ANALYSIS DOMAIN : INCLUDING DIVIDED DOMAINS OTHER THAN ORTHOGONAL GRID SHAPE | -CALCULATION DATA MODEL : NOT REQUIRING VERTEX AND CONNECTIVITY : REQUIRING POSITIONS OF PARTICLES AND LINKAGE RELATION BETWEEN PARTICLES -ANALYSIS DOMAIN : DIVIDED DOMAINS ARE ABSENT |
| SOLVER PROCESS | -PHYSICAL VALUE CALCULATION : NOT REQUIRING VERTEX AND CONNECTIVITY | -PHYSICAL VALUE CALCULATION : REQUIRING VERTEX AND CONNECTIVITY | -PHYSICAL VALUE CALCULATION : NOT REQUIRING VERTEX AND CONNECTIVITY : REQUIRING TIME-DEPENDENT NEAR-NEIGHBOR ALGORITHMS |

*FIG. 4*
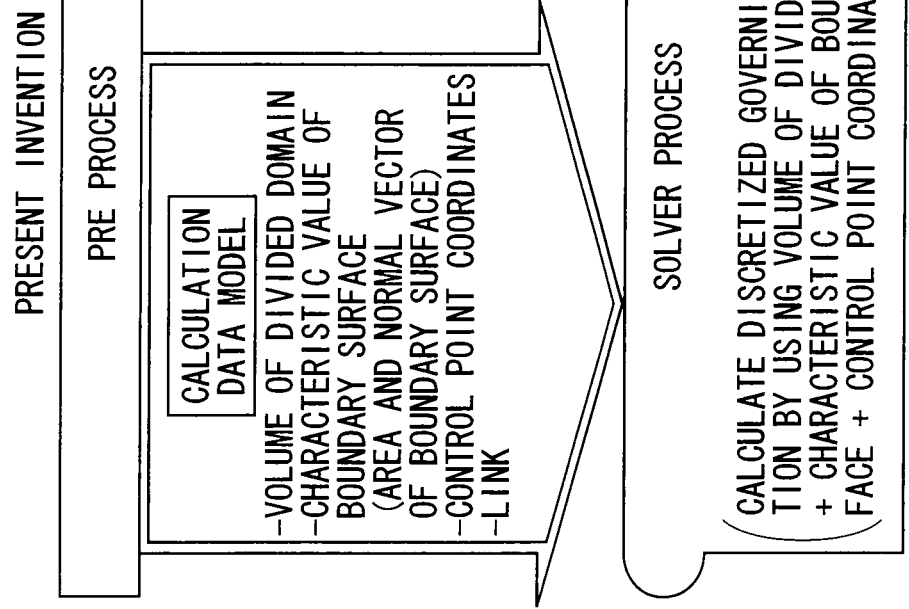
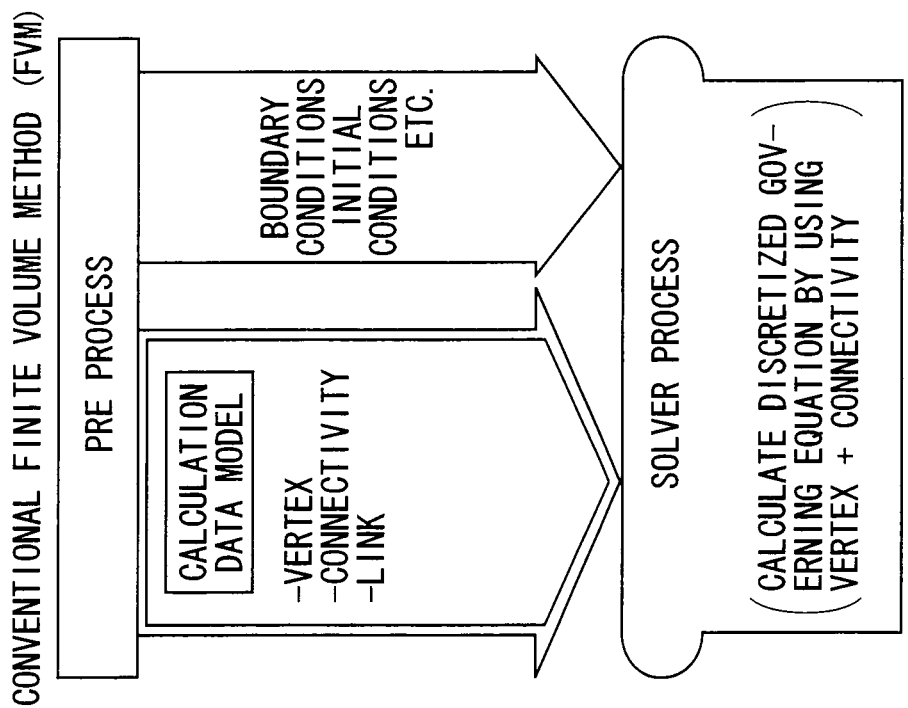

CALCULATION METHOD FOR PHYSICAL VALUE, NUMERICAL ANALYSIS METHOD, CALCULATION PROGRAM FOR PHYSICAL VALUE, NUMERICAL ANALYSIS PROGRAM, CALCULATION DEVICE FOR PHYSICAL VALUE, AND NUMERICAL ANALYSIS DEVICE

TECHNICAL FIELD

The present invention relates to a calculation method for physical value, a numerical analysis method, a calculation program for physical value, a numerical analysis program, a calculation device for physical value, and a numerical analysis device.

BACKGROUND ART

In the conventional art, as methods for numerical analysis for flow velocity distribution, stress distribution, heat distribution, and the like by numerical analysis, known techniques include a finite element method, a finite volume method, a voxel method, and a particle method.

In general, such a method for numerical analysis is constructed from pre process, solver process, and post process. Then, the pre process generates a calculation data model. Then, the solver process calculates the above-mentioned physical values by using the calculation data model and a governing equation having been discretized (referred to as a discretized governing equation, hereinafter).

In a conventional finite volume method, for example, the analysis domain is divided into a plurality of domains. Then, physical values in each divided domain are calculated by using the volume of each divided domain, the area of the boundary surface between adjacent divided domains, and the normal vector of the boundary surface.

In a finite volume method, the pre process generates a calculation data model (usually referred to as a mesh) containing the coordinates (Vertex) of the vertices of each divided domain. Then, the solver process calculates the volume of the above-mentioned divided domain, the area of the boundary surface, and the normal vector of the boundary surface by using the Vertex and the like contained in the calculation data model, and then calculates physical values by using these values. The Vertex indicates values for setting forth the geometric shape of the divided domain. Thus, it is recognized that in a finite volume method, the solver process calculates the volume of the divided domain, the area of the boundary surface, and the normal vector of the boundary surface by using the geometric shape of the divided domain.

Further, in a finite volume method, a part may be provided where the vertex sharing condition for adjacent divided domains is not partly satisfied. Thus, in a finite volume method, restriction on the divided domain is somewhat alleviated in some cases. Nevertheless, the element type for analysis to be used is limited to, for example, a tetra element, a hexa element, a prism element, and a pyramid element.

Here, as shown in Patent Document 1, a finite volume method without limit of element type for analysis has also been proposed. Nevertheless, even in such a finite volume method without limit of element type for analysis, similarly to a conventional finite volume method described above, the pre process generates a calculation data model containing the coordinates (Vertex) of the vertices of each divided domain and then the solver process calculates physical values by using the Vertex contained in the calculation data model.

Further, as known widely, the finite element method is a method of calculating the physical values in each divided domain by using an interpolation function. However, similarly to a finite volume method, the solver process uses the geometric shape of the divided domain set forth by the Vertex and the like.

The voxel method and the particle method are methods for numerical analysis capable of easily generating a calculation data model in comparison with a finite element method and a finite volume method.

The voxel method is a method that voxel data for defining the analysis domain by using a plurality of voxels (an orthogonal grid) having a rectangular parallelepiped shape and basically the same size is generated as a calculation data model and that physical value calculation is performed by using the voxel data so that numerical analysis is achieved. Voxel methods are schematically divided into: a weighted residual type that uses a governing equation based on a weighted residual method; and a non-integration type that uses a cellular automaton model, a lattice Boltzmann model, or the like. Then, according to this voxel method, Vertex and the like to be used as voxel data are unnecessary.

According to such a voxel method, the analysis domain is easily defined by dividing the analysis domain into voxels. Thus, a calculation data model is generated in a short time.

On the other hand, the particle method is a method that particle data is generated as a calculation data model for defining the analysis domain by a plurality of particles and that physical value calculation is performed by using this particle data so that numerical analysis is achieved. The particle method of non-integration type uses an inter-particle interaction model as a governing equation. The particle method does not have divided domains, and hence does not require Vertex and the like. Thus, according to such a particle method, the analysis domain is easily defined by arranging particles uniformly in the analysis domain, so that a calculation data model is generated in a short time.

PRIOR ART REFERENCE

Patent Document

Patent Document 1: U.S. Patent Application Publication No. 2008/0021684 Specification

SUMMARY OF THE INVENTION

Problems to be Solved by the Invention

In a case that the geometric shape of each divided domain is used in solver process like in a conventional method for numerical analysis such as a finite element method and a finite volume method, obviously, it is indispensable that the calculation data model has data describing the geometric shape of the divided domain.

For the purpose of defining the geometric shape of the divided domain, the vertex connectivity (Connectivity of Vertex; referred to as Connectivity, hereinafter) is necessary in addition to Vertex. Thus, in a finite element method and a finite volume method, it is necessary that the calculation data model has Vertex and Connectivity.

Here, specifically, Connectivity is defined by correspondence information of overall node numbers sequentially imparted to the vertices of all divided domains and local node numbers sequentially imparted to the vertices in one divided domain.

As known widely, a calculation data model having such Vertex and Connectivity requires remarkably enormous work for generation.

For example, in a calculation data model used in a finite element method, the calculation data model need be generated such that a condition should be satisfied that adjacent divided domains always share the Vertex as shown in FIG. 1. Thus, in order that all divided domains should satisfy this condition, remarkably enormous time is necessary.

On the other hand, in a calculation data model used in a finite volume method, the presence of Vertex not shared by adjacent divided domains is allowed as shown in FIG. 2. This increases the flexibility of mesh generation in comparison with a finite element method. Nevertheless, even in a finite volume method, the calculation data model need be generated on conditions that unshared Vertex is located at least on an edge of adjacent divided domains and that, in general, the shape of the divided domain agrees with the element type for analysis set up in advance. Thus, it is hard to say that the flexibility of mesh generation is high.

Further, in recent years, numerical analysis is performed on the analysis domain extracted from 3D shape data such as three-dimensional CAD (Computer Aided Design) data. Nevertheless, the 3D shape data is not data formed for numerical analysis. Thus, data is contained that indicates overlapping surfaces, surface intersection, gaps between surfaces, a small hole, and the like. That is, many conditions are included that are not suitable for generation of a calculation data model having Vertex and Connectivity. Thus, in order that a calculation data model having Vertex and Connectivity should be allowed to generate, the 3D shape data need be modified or changed. Then, in order that modification or change of the 3D shape data should be allowed for the purpose of generation of a calculation data model having Vertex and Connectivity, remarkably enormous manual work need be performed that requires experience and a trial and error approach. This causes a large problem at the time of practical use of a finite element method or a finite volume method.

Further, like in a finite volume method, in a case that the solver process calculates the volume of the divided domain, the area of the boundary surface, and the normal vector of the boundary surface, the amount of calculation increases further in the solver process so that computation load to the solver process increases further.

In a voxel method, the calculation data model can be generated in a short time. Nevertheless, the following problem arises. In a voxel method, the analysis domain is defined basically by voxels (an orthogonal grid) all having the same size. In general, in a finite element method and a finite volume method, the element size (the size of each divided domain) is set small in a domain where a higher accuracy of analysis is desired, so that the physical value calculation is achieved with precision in this domain. Further, the element size for the other domain is set large so that computation load for this domain is reduced. Nevertheless, in a voxel method, all voxels have basically the same size. Thus, when the voxels are set small, computation load becomes remarkably large. In contrast, when the voxels are set large, accuracy of analysis is degraded.

Further, in a voxel method, each analysis domain need be defined by arranging voxels (an orthogonal grid) having the same size. Thus, the analysis domain cannot be smooth near the boundary to an external domain and hence forms a stepwise shape in some cases. That is, even when an actual domain to be analyzed has an inclined plane, a curved surface, or the like, the domain is represented in a stepwise shape in the voxel data. Thus, the analysis domain shape in the voxel method becomes different from the actual domain shape to be analyzed. This degrades accuracy of analysis.

Thus, an improved method referred to as a cut-cell method has been proposed that the step-like domain in the voxel data is cut along the inclined plane or the curved surface (boundary correction) present in the actual domain to be analyzed. Nevertheless, in this improved method, the boundary correction easily generates remarkably small divided domains. Then, when such small divided domains are generated, accuracy of analysis is degraded.

Further, in this improved method, the cut cell generation and the solver process use Vertex.

As described above, a voxel method without boundary correction does not require Vertex and the like. Nevertheless, limit is present in voxel generation, that is, in so-called mesh generation. That is, when sufficient accuracy of analysis is required, the number of voxels increases and the computation load in the solver process also increases. This causes a problem. Further, in an improved method of voxel method with boundary correction, Vertex becomes necessary as a result. Thus, an influence is caused from the geometric shape of the divided domains. As a result, remarkably enormous manual work requiring experience and a trial and error approach becomes necessary for the processing of divided domain generation near the boundary to the external domain. Thus, the shape data model cannot be generated in a short time.

On the other hand, a particle method requires calculation of the linkage relation of a particular particle to other particles. Thus, particles present in the neighborhood of the particular particle need be searched for. Then, this particle near neighbor algorithms is performed on all particles in principle. Nevertheless, in the particle method, every particle moves time dependently and hence the linkage relation between particles varies always. Thus, the near neighbor algorithms need be performed at each time of change of the time in analysis. This causes an increase in the computation load. Thus, an attempt has been performed that particles on which the neighborhood search is to be performed are selected carefully so that the computation load in the near neighbor algorithms is reduced. Nevertheless, for example, when the number of particles is increased for the purpose of improvement of accuracy of analysis, the computation load increases in proportion to the square of the number of particles.

In such a particle method, in order that numerical analysis within a practical time should be realized, a large number of CPUs (Central Processing Units) in a large parallel processing machine need be used. For example, in an actual case, a calculation completed in half a day by a common finite volume method solver using Vertex and Connectivity on a single CPU took more than one week by a particle method employing parallel computation using 32 CPUs.

Further, even in a particle method, when particles are arranged densely, computation load increases remarkably. When particles are arranged coarsely, accuracy of analysis is degraded.

Further, as described later in detail, in a particle method, when a physical phenomenon such as fluid, structure, heat, and diffusion based on the conservation law for a physical value is analyzed, the conservation is not sufficiently satisfied.

For example, information concerning the area occupied on a boundary surface by a particle arranged such as to face the boundary surface between the analysis domain and the external domain is not present. Thus, even when a condition that heat is inputted through the boundary surface is desired to be placed, the amount of heat inputted to each particle is not recognized accurately. Thus, a precise quantitative value is not obtained.

The present invention has been devised in view of the problems in the conventional methods for numerical analysis described above like a finite element method, a finite volume method, a voxel method, an improved technique of voxel method, and a particle method. An object of the present invention is to reduce work burden in generation of a calculation data model and to reduce computation load in solver process without causing degradation in accuracy of analysis.

Solution to the Problems

In order to resolve the above-mentioned problem, the present invention employs a configuration of a calculation method for physical value for calculating physical values in a numerical analysis method for numerically analyzing a physical phenomenon, comprising a physical value calculation step of calculating physical values in an analysis domain divided into a plurality of divided domains not limited to an orthogonal grid shape, wherein in the physical value calculation step, the physical values are calculated by using: a discretized governing equation that uses values not requiring coordinates (Vertex) of vertices of the divided domains and connectivity information (Connectivity) of the vertices and that is derived on the basis of a weighted residual method; and a calculation data model in which volumes of the divided domains and characteristic values of boundary surface indicating characteristics of boundary surfaces of adjacent ones of the divided domains are provided as the values not requiring coordinates (Vertex) of vertices of the divided domains and connectivity information (Connectivity) of the vertices.

The discretized governing equation used in the present invention is not conventional one expressed in a form containing values (Vertex and Connectivity) that set forth the geometric shape of each divided domain, and is one not requiring values that set forth the geometric shape of each divided domain. The discretized governing equation used in the present invention is obtained by intentionally stopping, in the middle, the process of deriving, on the basis of a weighted residual method, a conventional equation using values that set forth the geometric shape. Such a discretized governing equation used in the present invention is expressed in values not requiring the geometric shape of the divided domain (i.e., values not requiring Vertex and Connectivity), and then may be expressed in a form, for example, depending solely on the two of the volume of the divided domain and the characteristic value of boundary surface.

That is, in a conventional finite element method or finite volume method, the object to be analyzed is divided into minute domains as a premise. Thus, the discretized governing equation is derived on a premise that values setting forth the geometric shape of each minute domain, that is, Vertex and Connectivity, are used. In contrast, the discretized governing equation used in the present invention is derived from a different and completely new way of thinking from the conventional art.

Then, the present invention is characterized by employing the discretized governing equation derived from such a new way of thinking. Thus, in contrast to the conventional numerical analysis method, the method according to the present invention resolves the conventional problems without depending on the geometric shape, and provides various kinds of remarkable effects.

Here, the fact is explained below that the volume of the divided domain and the characteristic value of boundary surface are values not requiring Vertex and Connectivity that set forth a particular geometric shape of the divided domain. Here, the values not requiring Vertex and Connectivity indicate values that can be defined without the use of Vertex and Connectivity.

For example, when the volume of a divided domain is considered, plural possibilities are present for the geometric shape of the divided domain whose volume takes a predetermined value. That is, the geometric shape of the divided domain whose volume takes a predetermined value may be a cube or a sphere. Then, for example, under the constraint that the total sum of all divided domains agrees with the volume of the entire analysis domain, the volumes of the divided domains may be defined by optimization calculation performed such that, for example, the volume of each divided domain should be proportional to the third power of the average distance from each adjacent divided domain as much as possible. Thus, the volume of the divided domain may be recognized as a quantity not requiring a particular geometric shape of the divided domain (a quantity not requiring Vertex and Connectivity).

Further, the characteristic value of boundary surface may be, for example, the area of the boundary surface, the normal vector of the boundary surface, or the contour length of the boundary surface. However, plural possibilities are present for the geometric shape of the divided domain (i.e., the geometric shape of the boundary surface) where the characteristic value of boundary surface has a predetermined value. Then, for example, under the constraint that the length of the area weighted average vector of the normal vector becomes zero for all boundary surfaces enclosing the divided domains, the characteristic value of boundary surface may be defined by optimization calculation performed such that the direction of the normal vector of the boundary surface is made close to the line segment that joins the control points of two adjacent divided domains (see FIG. 5) and that the total sum of the total boundary surface areas enclosing the divided domain should be proportional to the three-seconds power of the volume of the divided domain as much as possible. Thus, the characteristic value of boundary surface may be recognized as a quantity not requiring a particular geometric shape of the divided domain (a quantity not requiring Vertex and Connectivity).

Further, in the present invention, the description that "an analysis domain divided into a plurality of divided domains not limited to an orthogonal grid shape" indicates that at least one of the plurality of divided domains constituting the analysis domain does not have an orthogonal grid shape. That is, the description indicates that the analysis domain contains a divided domain having a shape other than an orthogonal grid shape.

Further, in the present invention, the description that "only values not requiring Vertex and Connectivity are used" indicates that values to be substituted into the discretized governing equation are only values not requiring Vertex and Connectivity.

Next, with reference to the conceptual diagram of FIG. 3, more detailed description is given below for the remarkable effects of the present invention by an approach of comparison of the pre process and the solver process in the method for numerical analysis using the present invention and in the conventional method for numerical analysis.

In the case of the method for numerical analysis using the present invention, as shown in FIG. 3, in the solver process (a physical value calculation step of the present invention), physical values in the divided domains are calculated by using a discretized governing equation that uses only values not requiring Vertex and Connectivity. Thus, at the time of solving the discretized governing equation, the calculation data model generated in the pre process need not contain Vertex and Connectivity.

Then, when the present invention is used, the volume of the divided domain and the characteristic value of boundary surface are used as values not requiring Vertex and Connectivity. Thus, the calculation data model generated in the pre process does not have Vertex and Connectivity but have the volume of the divided domain, the characteristic value of boundary surface, and other auxiliary data (e.g., linkage information of the divided domains and control point coordinates which are described later).

As such, when the present invention is used, as described above, physical values in each divided domain can be calculated on the basis of the volume of the divided domain and the above-mentioned characteristic value of boundary surface, that is, on the basis of values not requiring the geometric shape of the divided domain. Thus, physical values can be calculated in a state that the calculation data model does not have the geometric shape of the divided domain, that is, Vertex and Connectivity. Thus, when the present invention is used, in the pre process, it is sufficient that a calculation data model is generated that has at least the volume of the divided domain and the characteristic value of boundary surface (the area of the boundary surface and the normal vector of the boundary surface). Thus, physical values can be calculated without generating a calculation data model having Vertex and Connectivity.

The calculation data model not having Vertex and Connectivity does not require the geometric shape of the divided domain, and hence can be generated without restriction caused by the geometric shape of the divided domain.

Thus, restriction on correction work for the 3D shape data is also alleviated remarkably. Thus, the calculation data model not having Vertex and Connectivity can be generated far more easily than a calculation data model having Vertex and Connectivity. Thus, according to the present invention, work burden in generation of the calculation data model is reduced.

Further, even when the present invention is used, in pre process, Vertex and Connectivity may be used. That is, in the pre process, the volume of the divided domain, the characteristics of boundary surface, and the like may be calculated by using Vertex and Connectivity. Even in such a case, in the solver process, physical values can be calculated as long as the volume of the divided domain and the characteristics of boundary surface are available. Thus, even in a case that Vertex and Connectivity are used in the pre process, restriction on the geometric shape of the divided domain, for example, restriction caused by deformation, twist, or the like of the divided domain, is avoidable. This reduces work burden in generation of the calculation data model.

Further, when the present invention is used, in the pre process, restriction on the geometric shape of the divided domain is avoided. Thus, the divided domain may be changed into an arbitrary shape. Thus, the analysis domain can easily be fit to the actual domain to be analyzed without an increase in the number of divided domains. Thus, accuracy of analysis can be improved without an increase in the computation load.

Further, when the present invention is used, the density of distribution of the divided domains can also be changed arbitrarily. Thus, accuracy of analysis can also be improved further, with allowing an increase in the computation load to a necessary extent.

Further, when the present invention is used, in contrast to the conventional method for numerical analysis, in the solver process, calculation of the volume of the divided domain and the characteristic value of boundary surface need not use Vertex and Connectivity. Thus, computation load in the solver process can also be reduced.

Further, in the present invention, when the shape of the analysis domain does not vary, movement of the divided domains is unnecessary. Thus, near neighbor algorithms which need be performed at each time of change of the time in a particle method is unnecessary. Thus, computation load is small. Further, as described later in detail, when the present invention is used, in contrast to a particle method, physical values can be calculated in a state that the conservation laws for physical values are satisfied.

On the other hand, in a finite volume method which is a conventional method for numerical analysis, the pre process generates a calculation data model having Vertex and Connectivity expressing the geometric shape of the divided domain. Then, the solver process calculates the volume of the divided domain and the characteristic value of boundary surface (the area of the boundary surface and the normal vector of the boundary surface) by using Vertex and Connectivity contained in the calculation data model, and then calculates physical values in each divided domain. In this case, it is required that restriction on the geometric shape, that is, the relation between Vertex and Connectivity, does not cause a problem. Thus, the calculation data model (i.e., a mesh) need be generated within the restriction such as deformation and twist of the divided domain. This causes a problem of enormous manual work in the calculation data model generation as described above.

Further, also in a finite element method, the solver process calculates physical values by using Vertex and Connectivity contained in the calculation data model. Thus, the pre process need generate the calculation data model having Vertex and Connectivity expressing the geometric shape of the divided domain. Thus, enormous manual work arises in the calculation data model generation.

Further, in a voxel method which is a conventional method for numerical analysis, as shown in FIG. 3, at the time of calculating physical values in the solver process, Vertex and Connectivity are unnecessary. However, the shape of the divided domain is limited to a voxel. Thus, as described above, a problem arises that a boundary to an external domain has a stepwise shape. Thus, as described above, when sufficient accuracy of analysis is required, the number of voxels increases and the computation load in the solver process also increases. This causes a problem. Further, in a voxel method with boundary correction, finally, Vertex is used at the time of calculating the volume and the like of the divided domain. Thus, generation of the calculation data model is affected by the geometric shape of the divided domain.

Further, in a particle method which is a conventional method for numerical analysis, the concept of a divided domain is absent. Thus, as shown in FIG. 3, at the time of calculating physical values in the solver process, Vertex and Connectivity are unnecessary. However, the movement of particles that define the calculation data model in place of the divided domains causes an increase in computation load as described above. Further, in a particle method, calculation of physical values in a state that the conservation law is satisfied is difficult.

Next, with reference to FIG. 4, comparison between the present invention and the conventional finite volume method is given below in further detail.

In the conventional finite volume method, as described above, pre process generates a calculation data model having Vertex and Connectivity that define the geometric shape of the divided domain obtained by mesh dividing. Further, in general, the solver process requires linkage information (referred to as link, hereinafter) for the divided domain. Thus, the pre process generates a calculation data model having Vertex, Connectivity, and link.

Then, in the conventional finite volume method, as shown in FIG. 4, the calculation data model having Vertex, Connectivity, and link and a boundary condition, an initial condition, and the like necessary in the solver process are transferred from the pre process to the solver process. Then, the solver process solves the discretized governing equation by using the Vertex, Connectivity, and the like contained in the transferred calculation data model, and thereby calculates physical values.

On the other hand, in the present invention, the pre process generates a calculation data model having the volume of each divided domain arranged arbitrarily, the characteristic value of boundary surface (the area of the boundary surface and the normal vector of the boundary surface), and link. Further, as described later in detail, in the present invention, in some cases when necessary, the calculation data model is provided with the coordinates of the control point arranged in the inside of each divided domain.

Then, in the present invention, as shown in FIG. 4, the calculation data model having the volume of the divided domain, the characteristic value of boundary surface, and link (the coordinates of the control point, when necessary), a boundary condition, an initial condition, and the like are transferred from the pre process to the solver process. The solver process solves the discretized governing equation by using the volume of the divided domain, the characteristic value of boundary surface, and the like contained in the transferred calculation data model, and thereby calculates physical values.

Then, as seen from FIG. 4, an essential difference of the present invention from the conventional finite volume method is that the solver process calculates physical values without the use of Vertex and Connectivity. This point is a remarkable feature of the present invention. This feature results from the fact that the solver process uses a discretized governing equation that uses only values not requiring Vertex and Connectivity.

As a result, as shown in FIG. 4, in the present invention, Vertex and Connectivity need not be transferred to the solver process. Thus, it is sufficient that the pre process generates a calculation data model not having Vertex and Connectivity. Thus, in comparison with the conventional finite volume method, in the present invention, the calculation data model can be generated far more easily. Thus, work burden in generation of the calculation data model is reduced.

Further, in some cases, the shape of the analysis domain on which numerical analysis is to be performed varies time series, that is, the analysis domain includes a moving boundary. In such a case, the divided domains need be moved and deformed in accordance with the moving boundary.

In the conventional finite volume method, calculation of physical values in a case that a moving boundary is included is achieved by a method that Vertex at every movement of the moving boundary is stored in advance or alternatively by a method that domain dividing is re-executed when calculability is lost owing to extreme deformation of the divided domain. In contrast, in the present invention, calculation of physical values in a case that a moving boundary is included is achieved by a method that the volume of the divided domain, the characteristics of boundary surface, and the like in place of Vertex are calculated and stored in advance or alternatively by a method that domain dividing is re-executed.

In the conventional finite volume method or alternatively in the present invention, in a case that whichever of the above-mentioned methods is adopted, a plurality of calculation data models need be generated. Nevertheless, in the conventional finite volume method, in a situation that generation of merely a single calculation data model requires an enormous amount of work, generation of a plurality of models becomes unachievable within a range of practically available amount of work in many cases.

On the other hand, in the present invention, the calculation data model need not have Vertex and Connectivity and the consistency in Vertex and Connectivity need not be considered in the domain dividing processing. Thus, the calculation data model can be calculated at a remarkably high speed. Thus, physical values in a case that a moving boundary is included are calculated easily.

Here, supplementary description is given below for the above-mentioned link. The link is information describing relation between divided domains in which physical values are exchanged with each other. Then, the divided domains whose relation is described in this link need not be spatially adjacent to each other. That is, they may be spatially apart from each other. Such link is not connected to Vertex or Connectivity. Thus, in comparison with Vertex and Connectivity, the link can be generated in a remarkably short time.

Next, the principle of the method for numerical analysis (referred to as the present numerical analysis method, hereinafter) using the present invention, that is, the principle that physical values can be calculated by using a discretized governing equation derived on the basis of a weighted residual method and by using the volume of the divided domain and the characteristic value of boundary surface is described in detail. Here, in the following description, a character surrounded by [ ] indicates a vector represented in a bold font in the drawings.

First, the calculation data model in the present numerical analysis method is defined by using the volume of each divided domain obtained by dividing the analysis domain and the characteristic value of boundary surface indicating the characteristics of the boundary surface between adjacent divided domains.

FIG. 5 is a conceptual diagram showing an example of a calculation data model of the present numerical analysis method as described above.

In the figure, the cells $R_1$, $R_2$, $R_3$ . . . are divided domains obtained by dividing the analysis domain, and have volumes $V_a$, $V_b$, $V_c$ . . . , respectively. Further, the boundary surface E is a surface through which physical values are exchanged between the cell $R_1$ and the cell $R_2$, and corresponds to the boundary surface in the present invention. Further, the area $S_{ab}$ denotes the area of the boundary surface E, and is one of the characteristic values of boundary surface in the present invention. Further, $[n]_{ab}$ denotes the normal vector of the boundary surface E, and is one of the characteristic values of boundary surface in the present invention. Further, each of the control points a, b, c . . . is arranged in the inside of each of the cells $R_1$, $R_2$, and $R_3$. In FIG. 5, each control point is arranged at the position of the center of gravity of each of the cells $R_1$, $R_2$, $R_3$ . . . . However, each of the control points a, b, c . . . need not be arranged at the position of the center of gravity of each of the cells $R_1$, $R_2$, $R_3$ . . . . Further, $\alpha$ denotes the distance from the control point a to the boundary surface E in a case that the distance from the control point a to the control point b is defined to be 1. Thus, $\alpha$ is a ratio indicating an internally dividing point where the boundary surface E is located on the line segment joining the control point a and the control point b.

Here, a boundary surface is present between every adjacent cells, rather than only between cell $R_1$ and cells $R_2$. Then, the normal vector of the boundary surface and the area of the boundary surface are also provided for every boundary surface.

Then, the actual calculation data model is constructed as a data group having: arrangement data for the control points a, b, c . . . ; volume data indicating the volumes $V_a, V_b, V_c$ . . . of the cells $R_1, R_2, R_3$ . . . where the control points a, b, c . . . are located; area data indicating the area of each boundary surface; and normal vector data indicating the normal vector of each boundary surface.

That is, the calculation data model of the present numerical analysis method is defined by: the volumes $V_a, V_b, V_c$ . . . of the cells $R_1, R_2, R_3$ . . . ; the areas of the boundary surfaces which are the characteristic values of boundary surface indicating the characteristics of the boundary surfaces between adjacent cells $R_1, R_2, R_3$ . . . ; and the normal vectors of the boundary surfaces which are the characteristic values of boundary surface indicating the characteristics of the boundary surfaces between adjacent cells $R_1, R_2, R_3$ . . . .

Here, the cells $R_1, R_2, R_3$ . . . have the control points a, b, c . . . , respectively. Thus, the volumes $V_a, V_b, V_c$ . . . of the cells $R_1, R_2, R_3$ . . . may be recognized as the volumes of the spaces (control volumes) virtually occupied by the control points a, b, c . . . , respectively.

Further, when necessary, the calculation data model of the present numerical analysis method has ratio data containing each ratio α indicating an internally dividing point where each boundary surface is located on the line segment joining the control points located on both sides of the boundary surface.

The following description is given for an example of physical value calculation that the flow velocity in each cell (divided domain) of the analysis domain is calculated by using the above-mentioned calculation data model. Here, the flow velocity at each control point is recognized as the flow velocity in each cell.

First, in the present physical value calculation, in the present method for numerical analysis, in the case of fluid analysis, the Navier-Stokes equations expressed by the following equation (1) and the continuity equation expressed by the following equation (2) are used.

[Expression 1]

$$\frac{\partial}{\partial t}(\rho u_i) + \frac{\partial}{\partial x_j}(\rho u_j u_i) = -\frac{\partial P}{\partial x_i} + \frac{\partial}{\partial x_j}\left[\mu \frac{\partial u_i}{\partial x_j}\right] \quad (1)$$

[Expression 2]

$$\frac{\partial (\rho u_j)}{\partial x_j} = 0 \quad (2)$$

Here, in the equations (1) and (2), t denotes time, $x_i$ (i=1, 2, 3) denote coordinates in the Cartesian system, ρ denotes the density of fluid, $u_i$ (i=1, 2, 3) denote the flow velocity components of the fluid, P denotes the pressure, μ denotes the coefficient of viscosity of the fluid, and the subscripts i (i=1, 2, 3) and j (j=1, 2, 3) denote the direction components in the Cartesian coordinate system. Further, the summation notation is applied for the subscripts j.

Then, when the equations (1) and (2) are integrated over the volume of the control volume on the basis of a weighted residual method, the equation (1) is rewritten into the following equation (3) and the equation (2) is rewritten into the following equation (4).

[Expression 3]

$$\int_V \frac{\partial}{\partial t}(\rho u_i) dV + \int_S (n \cdot u) u_i dS = -\int_S n_i P dS + \int_S \mu \frac{\partial u_i}{\partial n} dS \quad (3)$$

[Expression 4]

$$\int_S \rho n \cdot u dS = 0 \quad (4)$$

Here, in the equations (3) and (4), V denotes the volume of the control volume, ∫VdV denotes the integration with respect to the volume V, S denotes the area of the control volume, ∫SdS denotes the integration with respect to the area S, [n] denotes the normal vector of S, $n_i$ (i=1, 2, 3) denote the components of the normal vector [n], and ∂/∂n denotes the normal derivative.

Here, for simplicity of description, the density ρ and the coefficient of viscosity μ of the fluid are set to be constant. However, the approach employing these constants here can be extended even for a case that the materials property values of the fluid vary with time, space, temperature, and the like.

Then, at the control point a in FIG. 5, the area $S_{ab}$ of the boundary surface E is discretized so that each equation is transformed into an approximated equation in the form of an algebraic equation. As a result, the equation (3) is rewritten into the following equation (5) and the equation (4) is rewritten into the following equation (6).

[Expression 5]

$$V_a \cdot \rho \frac{\partial u_i}{\partial t} + \sum_{b=1}^{m}[S_{ab} \cdot (n_{ab} \cdot u_{ab}) u_{iab}] = \\ -\sum_{b=1}^{m}[S_{ab} \cdot n_{iab} \cdot P_{ab}] + \sum_{b=1}^{m}\left[S_{ab} \cdot \mu \cdot \left(\frac{\partial u_i}{\partial n}\right)_{ab}\right] \quad (5)$$

[Expression 6]

$$\sum_{b=1}^{m}[S_{ab} \cdot (n_{ab} \cdot u_{ab})] = 0 \quad (6)$$

Here, $[n]_{ab}$, $[u]_{ab}$, $u_{iab}$, $n_{iab}$, $P_{ab}$, and $(\partial u_i/\partial n)_{ab}$ that have subscripts a and b are physical values on the boundary surface E between the control point a and the control point b. Further, $n_{iab}$ is a component of $[n]_{ab}$. Further, m is the number of all control points in a linkage relation with the control point a (a relation of having a boundary surface in between).

Then, when the equations (5) and (6) are divided by $V_a$ (the volume of the control volume of the control point a), the equation (5) is rewritten into the following equation (7) and the equation (6) is rewritten into the following equation (8).

[Expression 7]

$$\rho \frac{\partial u_i}{\partial t} + \sum_{b=1}^{m} \left[ \frac{S_{ab}}{V_a} \cdot (n_{ab} \cdot u_{ab}) u_{iab} \right] = \qquad (7)$$

$$-\sum_{b=1}^{m} \left[ \frac{S_{ab}}{V_a} \cdot n_{iab} \cdot P_{ab} \right] + \sum_{b=1}^{m} \left[ \frac{S_{ab}}{V_a} \cdot \mu \cdot \left( \frac{\partial u_i}{\partial n} \right)_{ab} \right]$$

[Expression 8]

$$\sum_{b=1}^{m} \left[ \frac{S_{ab}}{V_a} \cdot (n_{ab} \cdot u_{ab}) \right] = 0 \qquad (8)$$

Here, the following equation (9) is adopted.

[Expression 9]

$$\phi_{ab} \equiv \frac{S_{ab}}{V_a} \qquad (9)$$

Then, the equation (7) is rewritten into the following equation (10) and the equation (8) is rewritten into the following equation (11).

[Expression 10]

$$\rho \frac{\partial u_i}{\partial t} + \sum_{b=1}^{m} [\phi_{ab} \cdot (n_{ab} \cdot u_{ab}) u_{iab}] = \qquad (10)$$

$$-\sum_{b=1}^{m} [\phi_{ab} \cdot n_{iab} \cdot P_{ab}] + \sum_{b=1}^{m} \left[ \phi_{ab} \cdot \mu \cdot \left( \frac{\partial u_i}{\partial n} \right)_{ab} \right]$$

[Expression 11]

$$\sum_{b=1}^{m} [\phi_{ab} \cdot (n_{ab} \cdot u_{ab})] = 0 \qquad (11)$$

In the equations (10) and (11), each of $[u]_{ab}$, $u_{iab}$, $P_{ab}$, and $(\partial u_i/\partial n)_{ab}$ is obtained in approximation as a weighted average (a weighted average where upwind scheme is taken into consideration, in case of the advective term) of the physical value on the control point a and the control point b, and is determined depending on the distance and the direction between the control points a and b, the positional relation (the above-mentioned ratio α) with the boundary surface E located between them, and the direction of the normal vector of the boundary surface E. Here, $[u]_{ab}$, $u_{iab}$, $P_{ab}$, and $(\partial u_i/\partial n)_{ab}$ are values independent of the geometric shape of the boundary surface E (i.e., values not requiring Vertex and Connectivity that set forth the cell shape).

Further, $\phi_{ab}$ defined by the equation (9) is a quantity (area/volume), and hence is a quantity independent of the geometric shape of the control volume (i.e., values not requiring Vertex and Connectivity that set forth the cell shape).

That is, these equations (10) and (11) are operation formulas based on a weighted residual method in which the physical value can be calculated by using only values not requiring Vertex and Connectivity that set forth the cell shape.

Thus, when the above-mentioned calculation data model is generated prior to the physical value calculation (the solver process) and then the calculation data model and the discretized governing equations (10) and (11) are used in the physical value calculation, the flow velocity can be calculated in the physical value calculation completely without the use of the geometric shape of the control volume (i.e., Vertex and Connectivity that set forth the shape of the cell).

As such, the flow velocity can be calculated in the physical value calculation completely without using Vertex and Connectivity. Thus, the calculation data model need not have Vertex and Connectivity. Thus, at the time of generation of the calculation data model, restriction is not caused by the geometric shape of the cell and hence the shape of the cell can be set up arbitrarily. Thus, according to the present numerical analysis method, restriction on correction work for the 3D shape data can be alleviated remarkably as described above.

Here, at the time of actually solving the equations (10) and (11), the physical values such as $[u]_{ab}$ and $P_{ab}$ on the boundary surface E are interpolated in general by linear interpolation. For example, when the physical value at the control point a is denoted by $\psi_a$ and the physical value at the control point b is denoted by $\psi_b$, the physical value $\psi_{ab}$ on the boundary surface E is obtained by the following equation (12).

[Expression 12]

$$\psi_{ab} = \tfrac{1}{2}(\psi_a + \psi_b) \qquad (12)$$

Further, by using the ratio α indicating an internally dividing point where the boundary surface is located on the line segment that joins the control points located on both sides of the boundary surface, the physical value $\psi_{ab}$ can also be obtained by the following equation (13).

[Expression 13]

$$\psi_{ab} = (1-\alpha) \cdot \psi_a + \alpha \cdot \psi_b \qquad (13)$$

Thus, when the calculation data model has the ratio data describing the ratio α, the physical value on the boundary surface E can be calculated according to the equation (13) by using a weighted average corresponding to the distances from the control point a and from the control point b.

Further, equations (the Navier-Stokes equations or the like) for a continuum model contain 1st-order partial derivative (partial differentials) of first order as shown in the equation (1).

Here, as for the differential coefficients in the equations for a continuum model, the degree of differential is lowered by transforming a volume integration into a surface integral by using integration by parts, Gauss's divergence theorem, or the generalized Green's theorem. Thus, differential of 1st-order is made into differential of zero-order (a scalar value or a vector value).

For example, according to the generalized Green's theorem, when the physical value is denoted by $\psi$, the following equation (14) holds.

[Expression 14]

$$\int_V \frac{\partial \psi}{\partial x_i} dV = \int_S \psi n_i dS \qquad (14)$$

Here, in the equation (14), $n_i$ (i=1, 2, 3) denote the components of the i-direction of the unit normal vector [n] on the surface S.

As a result of transformation of a volume integration into a surface integral, the differential of 1st-order terms in the equation for continuum model are treated as scalar values or vector values on the boundary surface. Then, these values can be interpolated from the physical values at the individual control points by the above-mentioned linear interpolation or the like.

Further, as described later, a certain equation for continuum model contains a partial derivative of second order.

When the integrand in the equation (14) is differentiated by one-more order, the following equation (15) is obtained. Then, the second-order differential term in the equation for continuum model is rewritten into the following equation (16) on the boundary surface E by using transformation of a volume integration into a surface integral.

[Expression 15]

$$\int_V \frac{\partial^2 \psi}{\partial x_i \partial x_j} dV = \int_S \frac{\partial \psi}{\partial x_j} n_i dS = \int_S \frac{\partial \psi}{\partial n} n_i n_j dS \qquad (15)$$

[Expression 16]

$$\int_{S_{ab}} \frac{\partial \psi}{\partial n_{ab}} \cdot n_{iab} \cdot n_{jab} dS \qquad (16)$$

Here, in the equation (15), ∂/∂n denotes the normal direction differential. In the equation (16), ∂/∂$n_{ab}$ denotes the $[n]_{ab}$-direction differential.

That is, by virtue of transformation of a volume integration into a surface integral, the second-order differential term in the equation for continuum model takes the form of a product between the normal direction differential of the physical value ψ (the differential in the direction of the normal $[n]_{ab}$ to $S_{ab}$) and the components $n_{iab}$ and $n_{jab}$ of [n].

Here, ∂ψ/∂$n_{ab}$ in the equation (16) is approximated into the following equation (17).

[Expression 17]

$$\frac{\partial \psi}{\partial n_{ab}} = \frac{\psi_b - \psi_a}{r_{ab} \cdot n_{ab}} \qquad (17)$$

Here, an inter-control-point vector $[r]_{ab}$ between the control point a and the control point b is defined as the following equation (18) on the basis of the position vector $[r]_a$ of the control point a and the position vector $[r]_b$ of the control point b.

[Expression 18]

$$r_{ab} = r_b - r_a \qquad (18)$$

Thus, since the area of the boundary surface E is $S_{ab}$, the equation (16) is rewritten into the following equation (19). Thus, the equation (16) can be calculated by using this.

[Expression 19]

$$\int_{S_{ab}} \frac{\partial \psi}{\partial n_{ab}} \cdot n_{iab} \cdot n_{jab} dS = S_{ab} \cdot \frac{\psi_b - \psi_a}{r_{ab} \cdot n_{ab}} \cdot n_{iab} \cdot n_{jab} \qquad (19)$$

In the derivation of the equation (16), the following facts are recognized.

All linear partial differential equations can be expressed by a linear sum of terms constructed from a constant or from a first-order, second-order, or other-order partial derivative multiplied by a coefficient. In the equations (15) to (18), when the physical value ψ is replaced by the first-order partial derivative of ψ, the volume integration of a higher-order partial derivative can be calculated as the surface integral of a lower-order partial derivative as shown in the equation (14). Thus, when this procedure is repeated successively from the low-order partial differential, the partial derivatives in all terms contained in the linear partial differential equation can all be calculated from: the physical value ψ at the control point; $\psi_{ab}$ which is ψ on the boundary surface calculated according to the equation (12) or the equation (13); the inter-control-point distance obtained from the inter-control-point vector defined by the equation (18); the area $S_{ab}$ of the boundary surface E shown in the equation (5); and the components $n_{iab}$ and $n_{jab}$ of the normal vector shown in the equation (16). Next, in a non-linear partial differential equation, for example, a term consisting of a product between ψ and the first-order partial derivative of ψ or a term consisting of the square of the first-order partial derivative, each of which is a non-linear term shown in the equation (20), can be obtained by numerical calculation by iteration calculation. That is, the iteration calculation may be performed in such a manner that ψ and the first-order partial derivative in each term are approximated by the calculated values obtained at the one-step prior iteration calculation. According to such a method, all non-linear terms in the partial differential equation can be obtained by numerical calculation.

The description given above has been made for a particular case of equations for continuum model. However, as seen from the description given above, discretization not requiring Vertex and Connectivity is applicable to any other kinds of partial differential equations. Nevertheless, the conservation law requires another satisfaction condition. This point is described later.

[Expression 20]

$$\phi \cdot \frac{\partial \phi}{\partial x_i}, \left(\frac{\partial \phi}{\partial x_i}\right)^2 \qquad (20)$$

Here, in the present numerical analysis method, the physical value calculation does not require Vertex and Connectivity as described above. Thus, at the time of generation of a calculation data model (the pre process), in a case that the volume of the control volume and the area and the normal vector of the boundary surface are calculated without using Vertex and Connectivity, the flow velocity can be calculated by using the discretized governing equations shown in the equations (10) and (11) and completely not using the geometric shape of the control volume (i.e., the geometric shape of the cell).

However, in the present numerical analysis method, the volume of the control volume and the area and the normal vector of the boundary surface need not be calculated by not using the particular geometric shape of the control volume. That is, the solver process does not use Vertex and Connectivity. Thus, even if the particular geometric shape of the control volume, specifically, Vertex and Connectivity, were used, restriction concerning the divided domain, that is, restriction on the deformation or the twist of the divided domain, like in the conventional finite element method or finite volume method is absent. Thus, the calculation data model can be calculated easily as described above.

Next, In the present numerical analysis method, depending on the conditions, the above-mentioned normal vector may be replaced by the distance vector that joins the control volumes. The reason for this is described below.

In a case that the normal vector $[n]_{ab}$ of the boundary surface E shown in FIG. 5 is in the same direction as the distance vector $[r]_{ab}$ that joins the control point a and the control point b, the normal vector $[n]$ is expressed as the following equation (21).

[Expression 21]

$$n_{ab} = \frac{r_{ab}}{|r_{ab}|} \quad (21)$$

Thus, in a case that the normal vector $[n]_{ab}$ of the boundary surface E is in the same direction as the distance vector $[r]_{ab}$, when the equation (21) is substituted into the discretized governing equations shown in the equations (10) and (11), discretized governing equations in a case that the normal vector $[n]_{ab}$ is in the direction joining the control points a and b are obtained. That is, in a case that the boundary surface and the vector that joins the control points located on both sides of the boundary surface are orthogonal to each other, the normal vector in the discretized governing equations may be replaced by the distance vector.

According to such discretized governing equations, the normal vector $[n]_{ab}$ of the boundary surface E can be determined from only the position coordinates of the control point.

Further, when the boundary surface E and the distance vector are made close to be orthogonal as much as possible, precision in the physical value calculation is improved. Thus, when the normal vector is replaced by the distance vector, calculation precision is improved.

Further, arbitrariness in the normal vector may be fixed to the direction joining the control points.

However, in a case that the arbitrariness in the normal vector is lost, flexibility cannot be imparted to the orientation of the boundary surface in some cases. In such a case, in comparison with a case that the arbitrariness in the normal vector is present, restriction arises on the setting of the volume of the control volume and the boundary surface at the time of generation of the calculation data model. Further, in a case that the normal vector is replaced by the vector joining the control points, the distance vector is necessary and hence the coordinates of the control point are necessary for the purpose of calculating the distance vector. Thus, the calculation data model need have the coordinate data of the control point or alternatively the distance vector data. However, even in this case, in the present numerical analysis method, the physical value calculation does not require Vertex and Connectivity.

Next, for the purpose of clarifying the difference between the present invention and a particle method, a condition is described below that the conservation law for the physical value should be satisfied in the physical value calculation.

For example, as shown in FIG. 6, the cells $R_a$, $R_b$, $R_c$, and $R_d$ are considered that divide the L-shaped passage into four sections. Here, the control point a, b, c, and d arranged in the inside of the cells $R_a$, $R_b$, $R_c$, and $R_d$, respectively are located at the centers of the cells $R_a$, $R_b$, $R_c$, and $R_d$. Further, the flow velocity vector on each boundary surface is assumed to be perpendicular to the boundary surface.

Here, in FIG. 6, $V_a$ is the volume of the cell $R_a$ (the volume of the control volume of the control point a), $V_b$ is the volume of the cell $R_b$ (the volume of the control volume of the control point b), $V_c$ is the volume of the cell $R_c$ (the volume of the control volume of the control point c), $V_d$ is the volume of the cell $R_d$ (the volume of the control volume of the control point d), $\rho_a$ is the density in the cell $R_a$, $\rho_b$ is the density in the cell $R_b$, $\rho_c$ is the density in the cell $R_c$, $\rho_d$ is the density in the cell $R_d$, Sa is the area of the boundary surface between the cell $R_a$ and the external domain, $S_c$ is the area of the boundary surface between the cell $R_c$ and the external domain, $S_d$ is the area of the boundary surface between the cell $R_d$ and the external domain, $S_{ab}$ is the area of the boundary surface between the cell $R_a$ and the cell $R_b$, $S_{ac}$ is the area of the boundary surface between the cell $R_a$ and the cell $R_c$, $S_{bd}$ is the area of the boundary surface between the cell $R_b$ and the cell $R_d$, $S_{cd}$ is the area of the boundary surface between the cell $R_c$ and the cell $R_d$, $u_a$ is the flow velocity on the boundary surface between the cell $R_a$ and the external domain, $u_c$ is the flow velocity on the boundary surface between the cell $R_c$ and the external domain, $u_d$ is the flow velocity on the boundary surface between the cell $R_d$ and the external domain, $u_{ab}$ is the flow velocity on the boundary surface between the cell $R_a$ and the cell $R_b$, $u_{ac}$ is the flow velocity on the boundary surface between the cell $R_a$ and the cell $R_c$, $u_{bd}$ is the flow velocity on the boundary surface between the cell $R_b$ and the cell $R_d$, $u_{cd}$ is the flow velocity on the boundary surface between the cell $R_c$ and the cell $R_d$, $\rho_a$ is the density in the cell $R_a$, $\rho_{ab}$ is the density on the boundary surface between the cell $R_a$ and the cell $R_b$, $\rho_{ac}$ is the density on the boundary surface between the cell $R_a$ and the cell $R_c$, and $\rho_{bd}$ is the density on the boundary surface between the cell $R_b$ and the cell $R_d$.

Discretization of the mass conservation equation is considered at the four control points a, b, c, and d (in the four cells $R_a$, $R_b$, $R_c$, $R_d$) shown in FIG. 6. Here, the discretized governing equation obtained by discretizing the mass conservation equation is given in the later-described equation (43).

The discretized governing equation at the control point a is shown in the following equation (22).

[Expression 22]

$$V_a \cdot \frac{\partial \rho_a}{\partial t} + [-S_a \cdot \rho_a \cdot u_a + S_{ab} \cdot \rho_{ab} \cdot u_{ab} + S_{ac} \cdot \rho_{ac} \cdot u_{ac}] = 0 \quad (22)$$

The discretized governing equation at the control point b is shown in the following equation (23).

[Expression 23]

$$V_b \cdot \frac{\partial \rho_b}{\partial t} + [-S_{ab} \cdot \rho_{ab} \cdot u_{ab} + S_{bd} \cdot \rho_{bd} \cdot u_{bd}] = 0 \quad (23)$$

The discretized governing equation at the control point c is shown in the following equation (24).

[Expression 24]

$$V_c \cdot \frac{\partial \rho_c}{\partial t} + [-S_c \cdot \rho_c \cdot u_c - S_{ac} \cdot \rho_{ac} \cdot u_{ac} + S_{cd} \cdot \rho_{cd} \cdot u_{cd}] = 0 \quad (24)$$

The discretized governing equation at the control point d is shown in the following equation (25).

[Expression 25]

$$V_d \cdot \frac{\partial \rho_d}{\partial t} + [-S_{cd} \cdot \rho_{cd} \cdot u_{cd} - S_{bd} \cdot \rho_{bd} \cdot u_{bd} + S_d \cdot \rho_d \cdot u_d] = 0 \quad (25)$$

Then, when the equations (22) to (25) are added together, the following equation (26) is obtained.

[Expression 26]

$$\left[V_a\frac{\partial \rho_a}{\partial t} + V_b\frac{\partial \rho_b}{\partial t} + V_c\frac{\partial \rho_c}{\partial t} + V_d\frac{\partial \rho_d}{\partial t}\right] + [\quad\quad (26)$$
$$-S_a\cdot\rho_a\cdot u_a - S_c\cdot\rho_c\cdot u_c + S_d\cdot\rho_d\cdot u_d] = 0$$

On the basis of the fact that the volumes $V_a, V_b, V_c,$ and $V_d$ of the control volumes of the control points a, b, c, and d are constant with respect to time, the volumes are moved into the time differential terms. Then, the equation (26) is rewritten into the following equation (27).

[Expression 27]

$$\frac{\partial}{\partial t}(\rho_a V_a + \rho_b V_b + \rho_c V_c + \rho_d V_d) + [\quad\quad (27)$$
$$-S_a\cdot\rho_a\cdot u_a - S_c\cdot\rho_c\cdot u_c + S_d\cdot\rho_d\cdot u_d] = 0$$

Here, when the total volume occupied by the control volumes of the control points a, b, c, and d, are denoted by $V_{abcd}$ and the mean density is denoted by $\bar{\rho}_{abcd}$, the total volume $V_{abcd}$ is expressed by the following equation (28) and the mean density $\bar{\rho}_{abcd}$ is expressed by the following equation (29).

[Expression 28]

$$V_{abcd} = V_a + V_b + V_c + V_d \quad\quad (28)$$

[Expression 29]

$$\bar{\rho}_{abcd} \equiv \frac{\rho_a V_a + \rho_b V_b + \rho_c V_c + \rho_d V_d}{V_{abcd}} \quad\quad (29)$$

Thus, the equation (27) is rewritten into the following equation (30).

[Expression 30]

$$V_{abcd}\cdot\frac{\partial \bar{\rho}_{abcd}}{\partial t} + [-S_a\cdot\rho_a\cdot u_a - S_c\cdot\rho_c\cdot u_c + S_d\cdot\rho_d\cdot u_d] = 0 \quad\quad (30)$$

The equation (30) indicates the fact that the difference between the in-following mass flux into the entire domain occupied by the control volumes of the control points a, b, c, and d and the out-flowing mass flux is equal to the change per unit time in the mean density (the mass change with respect to time) in the entire domain occupied by the control volumes of the control points a, b, c, and d. That is, the mass conservation equation discretized at each of the control points a, b, c, and d holds also in the domain occupied by the control volumes of all control points.

That is, when each discretized governing equation in the control volume domain indicated by a control point is added up for all control points, an equation must be obtained that satisfies the conservation law for the entire domain of the analysis domain serving as a calculation object.

Then, when the total number of control points is denoted by N and the equations of mass conservation shown in the equation (43) are added up, the following equation (31) is obtained.

[Expression 31]

$$\sum_{a=1}^{N}\left[V_a\frac{\partial \rho_a}{\partial t} + \sum_{b=1}^{m}\{S_{ab}\cdot\rho_{ab}\cdot(n_{ab}\cdot u_{ab})\}\right] = 0 \quad\quad (31)$$

In the equation (31), the area of the boundary surface between the control points is assumed to be identical when viewed from the control point a side and when viewed from the control point b side. Thus, the mass flux $(\rho[n]\cdot[u])\cdot S$ between the control points has an opposite sign of positive or negative and has the same absolute value on the control point a side and on the control point b side. Thus, the mass flux sum is canceled out into zero. That is, the equation (31) indicates that the difference between the in-flowing mass and the out-flowing mass in the entire domain to be calculated is equal to the mass change per unit time in the entire domain. Thus, the equation (31) serves as the mass conservation equation in the entire analysis domain.

Thus, in order that the equation (31) should satisfy the law of mass conservation in the entire domain to be calculated, necessary are: a condition that the area of the boundary surface is identical between the two control points; and a condition that the normal vector has the same absolute value when viewed from one control point side and when viewed from the other control point side.

Further, in order that the law of mass conservation should be satisfied, a condition is necessary that the volume occupied by the control volumes of all control points agrees with the total volume of the analysis domain as shown in the following equation (32).

[Expression 32]

$$V_{total} = \sum_{a=1}^{N} V_a \quad\quad (32)$$

This fact is easily recognized since the density $\rho$ of the continuum is expressed by a single variable $\rho 1 = \rho 2 = \ldots = \rho$.

As such, in order that the law of mass conservation should be satisfied, a condition is necessary that the total sum of the volumes of the control volumes of all control points agrees with the volume of the analysis domain.

Here, description has been given for the mass conservation equation. However, the conservation law need be satisfied also for the momentum and the energy of the continuum. Thus, also for these physical values, in order that the conservation law should be satisfied when each of later-described equations (50) and (55) is added up for all control points, necessary are: a condition that the volume occupied by the control volumes of all control points agrees with the total volume of the analysis domain; a condition that the area of the boundary surface is identical between two control points; and the normal vector has the same absolute value (in an opposite sign of positive or negative) when viewed from one control point side and when viewed from the other control point side.

Further, in order that the conservation law should be satisfied, in a case that the control volume occupied by the control point a is considered as shown in FIG. 7, a condition is necessary that the following equation (33) holds when an infinitely large projection plane P that passes through the control point a and that has a unit normal vector $[n]_p$ in an arbitrary direction is considered.

[Expression 33]

$$\sum_{i=1}^{m} [(n_i \cdot n_P) \cdot S_i] = 0 \tag{33}$$

Here, in FIG. 7 and in the equation (33), $S_i$ is the area of the boundary surface $E_i$, $[n]_i$ is the unit normal vector of the boundary surface $E_i$, and m is the total number of surfaces of the control volume.

The equation (33) indicates that the polyhedron constituting the control volume forms a closure space. This equation (33) holds even when a part of the polyhedron constituting the control volume is concave.

Here, as shown in FIG. 8, the equation (33) holds also for a triangle in two dimensions. Further, when limit is taken such that one surface of the polyhedron is made into an infinitesimal surface dS and then m is made ∞, the following equation (34) is obtained. This holds even for a closure curved surface object as shown in FIG. 9.

[Expression 34]

$$\int_S n \cdot n_P dS = 0 \tag{34}$$

The condition that the equation (33) holds is necessary for a condition that Gauss's divergence theorem or the generalized Green's theorem shown in the equation (14) holds.

Then, the generalized Green's theorem is a theorem providing the basis for the discretization of the continuum. Thus, in a case that a volume integration is changed into a surface integral according to the theorem of green and then discretization is performed, the condition that the equation (33) holds is indispensable in order that the conservation law should be satisfied.

As such, at the time of performing numerical analysis by using the calculation data model and the physical value calculation described above, the following three conditions are necessary in order that the conservation law for the physical value should be satisfied.

(a) The total of the volumes of the control volumes of all control points (the volume of all divided domains) agrees with the volume of the analysis domain.

(b) The area of the boundary surface is identical between two control points and the normal vector has the same absolute value when viewed from one control point side (one of the divided domains located on both sides of the boundary surface) and when viewed from the other control point side (the other one of the divided domains located on both sides of the boundary surface).

(c) The equation (33) holds when an infinitely large projection plane P that passes through the control point (passes through the divided domain) and that has a unit normal vector $[n]_p$ in an arbitrary direction is considered.

That is, when the conservation law is desired to be satisfied, the calculation data model need be generated such that these conditions are satisfied. However, as described above, in the present numerical analysis method, at the time of generation of the calculation data model, the cell shape can be deformed arbitrarily. Thus, the calculation data model can easily be generated such that the above-mentioned three conditions are satisfied.

Described below in detail are: the reason that an MPS (Moving Particle Semi-Implicit) method which is a conventional particle method cannot satisfy the conservation law; the reason of an increase in the computation load; and an advantage of the present method for numerical analysis over the particle method.

The MPS method is a technique that particles present within a sphere of radius $r_e$ set up appropriately are detected, then a linkage relation with each particle is established, and then calculation is performed. For example, as shown in FIG. 10, when a plurality of particles j are present around a particle i, the Laplacian $(\nabla^2 \psi)_i$ for the particle i is approximated as the following equation (35).

[Expression 35]

$$(\nabla^2 \phi)_i = \frac{2d}{m} \cdot \sum_{j \neq i}^{m} \left[ \frac{\psi_j - \psi_i}{|r_{ij}|^2} \cdot \omega(r) \right] \tag{35}$$

Here, in FIG. 10, $\psi_i$ denotes the physical value at the particle i, $\psi_j$ denotes the physical value at the particle j, and $[r]_{ij}$ denotes the distance vector from the particle i to the particle j.

Further, d in the equation (35) denotes the constant indicating the dimension, and hence is equal to three in a case of three dimensions. Further, $\omega(r)$ in the equation (35) is a weight function expressed by the following equation (36). Further, m in the equation (35) is the number of particles in the linkage relation.

[Expression 36]

$$\omega(r) = \begin{cases} \frac{r_e}{r} - 1 & (0 \leq r \leq r_e) \\ 0 & (r_e \leq r) \end{cases} \tag{36}$$

On the other hand, as shown in FIG. 11, in a case that the particles i and j are recognized as control points, that the control volume of the particle i is $V_i$, that the area of the boundary surface between the particle i and the particle j is $S_{ij}$, that the normal vector of the boundary surface between the particle i and the particle j is $[n]_{ij}$, and that the distance vector from the particle i to the particle j is $[r]_{ij}$, the Laplacian $(\nabla^2 \psi)_i$ for the particle i is approximated as the following equation (37).

[Expression 37]

$$(\nabla^2 \psi)_i = \frac{1}{V_i} \cdot \sum_{j \neq i}^{m} \left[ \frac{\psi_j - \psi_i}{|r_{ij} \cdot n_{ij}|} \cdot S_{ij} \right] \tag{37}$$

Then, when the equation (36) and the equation (37) are compared with each other, in a case that $[r]_{ij}$ and $[n]_{ij}$ are tentatively in the same direction, the following equations (38) and (39) are obtained.

[Expression 38]

$$\frac{S_{ij}}{V_i} \cdot \frac{1}{|r_{ij} \cdot n_{ij}|} = \frac{2d}{m} \cdot \frac{\omega(r)}{|r_{ij}|^2} \quad (38)$$

[Expression 39]

$$\frac{S_{ij}}{V_i} = \frac{2d}{m} \cdot \frac{\omega(r)}{|r_{ij}|} \quad (39)$$

The dimension is identical (1/distance) in the left side and in the right-hand side of the equation (39). Thus, the formulation of the MPS method may be interpreted as a technique that the quantity of (area/volume) (i.e., the ratio defined by the equation (9)) in the right-hand side shown in the following equation (40) is calculated from only the distance between two particles i and j.

[Expression 40]

$$\phi_{ij} = \frac{S_{ij}}{V_i} \quad (40)$$

Nevertheless, even when the area $S_{ij}$ of the boundary surface and the volume $V_i$ are desired to be calculated from the linkage relation of the m particles, a relational equation is insufficient. Thus, a particular numerical value cannot be determined and hence the ratio in the equation (40) is solely determined.

Thus, if the area $S_{ij}$ of the boundary surface and the volume $V_i$ were calculated from the discretized governing equation of the MPS method, it is not guaranteed that the above-mentioned conditions (a) to (c) necessary for satisfaction of the conservation law are satisfied. This indicates that the MPS method has a large problem in satisfaction of the conservation law.

In a case that numerical analysis is applied to a problem in engineering, especially, to a mechanical design problem or a plant design problem, evaluation of quantitative values (the pressure, the temperature, the heat amount, and the like) is remarkably important. Nevertheless, when the numerical analysis does not satisfy the conservation law, the fixedness is not guaranteed.

That is, in the MPS method, satisfaction of conservation laws such as mass conservation, momentum conservation, and energy conservation is not guaranteed and hence quantification is not guaranteed.

In contrast, according to the present numerical analysis method, conservation laws are satisfied and hence the fixedness is guaranteed.

Here, in the MPS method, as described above, the particles move in association with the change of time. Thus, for example, near neighbor algorithms need be performed that particles present within the above-mentioned sphere of radius $r_e$ are detected. This causes large computation load in the physical value calculation.

In contrast, in the present numerical analysis method, the control volume and the control point do not move even when time varies. Thus, in a case that the arrangement relation of the control volumes and the control points is known in advance, the physical value calculation is achieved without near neighbor algorithms. This reduces computation load in the physical value calculation in comparison with the MPS method. Here, even in a case that the arrangement relation of the control volumes and the control points is not known in advance, it is sufficient that the processing of defining the arrangement relation of the control volumes and the control points is performed only once in the beginning.

The description given above has been made for an example of physical value calculation using a discretized governing equation derived from the Navier-Stokes equations and the continuity equation on the basis of a weighted residual method. However, the discretized governing equation to be used in the present numerical analysis method is not limited to this.

That is, any discretized governing equation that is derived from various kinds of equations (such as the mass conservation equation, the equation for conservation of momentum, the equation for conservation of energy, the advection diffusion equation, and the wave equation) on the basis of a weighted residual method and that can calculate physical values by using only values not requiring Vertex and Connectivity may be used in the present numerical analysis method.

Then, by virtue of such characteristics of the discretized governing equation, calculation is achieved by a meshless approach that does not require a so-called mesh which is required by the conventional finite element method or finite volume method. Further, even if Vertex and Connectivity that set forth the geometric shape of the cell were used in the pre process, restriction on the mesh is absent in contrast to a finite element method, a finite volume method, and a voxel method according to the conventional art. This reduces work load associated with generation of the calculation data model.

Described below is the fact that a discretized governing equation that uses only values not requiring Vertex and Connectivity can be derived from the mass conservation equation, the equation for conservation of momentum, the equation for conservation of energy, the advection diffusion equation, and the wave equation on the basis of a weighted residual method, that is, the fact that the present numerical analysis method can employ other governing equations.

(1) Mass Conservation Equation

The mass conservation equation in the Euler coordinate system is expressed in a differential form as the following equation (41).

[Expression 41]

$$\frac{\partial \rho}{\partial t} + \frac{\partial \rho u_i}{\partial x_i} = 0 \quad (41)$$

Here, in the equation (41), t is time, $x_i$ (i=1, 2, 3) are coordinates in the Cartesian system, $\rho$ is density, $u_i$ (i=1, 2, 3) are the components of deformation rate, and subscript i (i=1, 2, 3) are direction components in the Cartesian coordinate system. Further, the summation notation is applied for the subscript i.

Then, when the equation (41) is integrated over the volume V of the control volumes of the control points on the basis of a weighted residual method, the following equation (42) is obtained.

[Expression 42]

$$\int_V \frac{\partial \rho}{\partial t} dV + \int_S \rho n \cdot u dS = 0 \quad (42)$$

Further, descretizing the equation for the control point a shown in FIG. 5 so as to transform it into an algebraic equation, the following equation (43) is obtained.

[Expression 43]

$$V_a \cdot \frac{\partial \rho_a}{\partial t} + \sum_{b=1}^{m} [S_{ab} \cdot \rho_{ab} \cdot (n_{ab} \cdot u_{ab})] = 0 \quad (43)$$

Here, $\rho_{ab}$ and $[n]_{ab}$ that have subscripts a and b are physical values on the boundary surface E between the control point a and the control point b. Further, m is the number of all control points in a linkage relation with the control point a (a relation of having a boundary surface in between).

Then, when the equation (43) is divided by $V_a$ which is the volume of the control volume of the control point a, the following equation (44) is obtained. Then, when the following equation (45) is adopted, the following equation (46) is obtained in which the mass conservation equation is discretized.

[Expression 44]

$$\frac{\partial \rho_a}{\partial t} + \sum_{b=1}^{m} \left[ \frac{S_{ab}}{V_a} \cdot \rho_{ab} \cdot (n_{ab} \cdot u_{ab}) \right] = 0 \quad (44)$$

[Expression 45]

$$\phi_{ab} = \frac{S_{ab}}{V_a} \quad (45)$$

[Expression 46]

$$\frac{\partial \rho_a}{\partial t} + \sum_{b=1}^{m} [\phi_{ab} \cdot \rho_{ab} \cdot (n_{ab} \cdot u_{ab})] = 0 \quad (46)$$

Such an equation (46) is an equation that is derived on the basis of a weighted residual method and that uses only values not requiring Vertex and Connectivity. Thus, such an equation may be used as a discretized governing equation in the present numerical analysis method.

Here, as described above, the discretized governing equation used in the present invention is obtained by intentionally stopping, in the middle, the process of deriving, on the basis of a weighted residual method, a conventional equation using values that set forth the geometric shape.

That is, the equation (46) is obtained in the process that the mass conservation equation is derived as an equation that uses Vertex and the like, on the basis of a weighted residual method.

Here, FIG. 12 is a schematic diagram showing a cell having a two-dimensional triangular shape. The area, the length of side, and the normal vector of the triangle a in FIG. 12 are shown in the following table. Here, symbol × in the following table denotes a cross product.

TABLE 1

| | |
|---|---|
| Area of triangle a | $\frac{1}{2}|r_{12} \times r_{13}|$ |
| Length of side $\bar{i}$ | $|r_{i+1} - r_i| = |r_{ii+1}|$ |

TABLE 1-continued

| | |
|---|---|
| Normal vector | $\frac{r_{ii+1} \times (r_i \times r_{i+1})}{|r_{ii+1} \times (r_i \times r_{i+1})|}$ |

As shown in FIG. 12, when the cell has a two-dimensional triangular shape, the mass conservation equation is transformed into a discretized governing equation that uses Vertex and the like, on the basis of a weighted residual method, the following equation (47) is obtained.

[Expression 47]

$$\frac{\partial \rho_a}{\partial t} + \sum_{b=1}^{3} \left[ \frac{|r_{bb+1}|}{|r_{12} \times r_{13}|} \cdot \frac{r_{bb+1} \times (r_b \times r_{b+1})}{|r_{bb+1} \times (r_b \times r_{b+1})|} \cdot \rho(u_a + u_b) \right] = 0 \quad (47)$$

Here, in the equation (47), $[r]_i$ is the position vector (coordinates) of the vertex (Vertex)$_i$, and symbol × denotes the cross product of vectors. Further, $\rho_{ab}$ and $\rho$ are fixed, $[r]_{ij}$ is equal to $[r]_j - [r]_i$, and $[r]_4$ is identical to $[r]_1$.

(2) Equation for Conservation of Momentum

The equation for conservation of momentum in the Euler coordinate system is expressed in a differential form as the following equation (48).

[Expression 48]

$$\frac{\partial}{\partial t}(\rho u_i) + \frac{\partial}{\partial x_j}(\rho u_j u_i) = \frac{\partial \sigma_{ij}}{\partial x_j} + \rho f_i \quad (48)$$

Here, in the equation (48), $\sigma_{ij}$ (i, j=1, 2, 3) indicate an internal stress in the continuum and $f_i$ (i=1, 2, 3) indicate an external force (such as gravitation) acting on the continuum. The other values are similar to those in the equation (41). Further, the summation notation is applied for the subscripts j.

This equation (47) is a basic equation for a stress field in a structure, a material, a fluid, or the like.

Then, when the equation (47) is integrated over the volume V of the control volumes of the control points on the basis of a weighted residual method, the following equation (49) is obtained.

[Expression 49]

$$\int_V \frac{\partial \rho}{\partial t}(\rho u_i)dV + \int_S \rho(n \cdot u)u_i dS = \int_S \sigma_{ij} \cdot n_j dS + \int_V \rho f_i \cdot dV \quad (49)$$

Further, descretizing the equation for the control point a shown in FIG. 5 so as to transform it into an algebraic equation, the following equation (50) is obtained.

[Expression 50]

$$V_a \cdot \frac{\partial \rho_a u_{ia}}{\partial t} + \sum_{b=1}^{m} [S_{ab} \cdot \rho \cdot (n_{ab} \cdot u_{ab}) u_{iab}] = \quad (50)$$

$$\sum_{b=1}^{m} [S_{ab} \cdot \sigma_{ijab} n_{jab}] + V_a \cdot f_{ia} \cdot \rho_a$$

When the equation (50) is divided by $V_a$ which is the volume of the control volume of the control point a and then the equation (45) is adopted, the following equation (51) is obtained in which the equation for conservation of momentum is discretized.

[Expression 51]

$$\frac{\partial \rho_a u_{ia}}{\partial t} + \sum_{b=1}^{m} [\phi_{ab} \cdot \rho \cdot (n_{ab} \cdot u_{ab}) u_{iab}] = \sum_{b=1}^{m} [\phi_{ab} \cdot \sigma_{ijab} n_{jab}] + f_{ia} \cdot \rho \quad (51)$$

Here, when the symmetry in the stress tensor is taken into consideration in the equation for conservation of momentum, the equation of conservation of angular momentum can also be discretized similarly to the equation for conservation of momentum.

(3) Advection Diffusion Equation

An advection diffusion phenomenon of a particular substance C into a continuum is expressed by the advection diffusion equation shown in the following equation (52).

[Expression 52]

$$\frac{\partial}{\partial t}(\rho C) + \frac{\partial}{\partial x_j}(\rho u_j C) = \frac{\partial}{\partial x_j}\left[\mu_C \frac{\partial C}{\partial x_j}\right] + \rho \cdot q_C \quad (52)$$

Here, in the equation (52), C is the concentration of the substance C, $\mu_c$ is the diffusion coefficient of the substance C, $q_c$ is the source (sink) term for the substance C, $\rho$ is the density of the continuum, and $u_i$ denotes the deformation rate of the continuum.

Then, when the equation (52) is integrated on the basis of a weighted residual method and then discretized and transformed into a discretized governing equation, the following equation (53) is obtained.

[Expression 53]

$$\frac{\partial \rho_a C_a}{\partial t} + \sum_{b=1}^{m} [\phi_{ab} \cdot \rho \cdot (n_{ab} \cdot u_{ab}) \cdot C_{ab}] = \quad (53)$$

$$\sum_{b=1}^{m} \left[\phi_{ab} \cdot \mu_C \cdot \left(\frac{\partial C}{\partial n}\right)_{ab}\right] + V_a \cdot \rho_a \cdot q_{Ca}$$

Here, values such as Ca having subscript a are physical values at the control point a. Values such as $C_{ab}$ having subscripts ab are physical values on the boundary surface between the control point a and the control point b.

(4) Equation for Conservation of Energy

The law of energy conservation is divided into the conservation of heat energy and the conservation of kinetic energy. However, the conservation of kinetic energy is included in the above-mentioned momentum conservation. Thus, here, a general form of the equation of conservation of heat energy is shown in the following equation (54).

[Expression 54]

$$\frac{\partial \rho U}{\partial t} + \frac{\partial}{\partial x_j}(\rho u_i \cdot U) = -\frac{\partial q_j}{\partial x_j} + \rho \cdot r + \sigma_{ij} \cdot D_{ij} \quad (54)$$

Here, in the equation (54), U is the internal energy of the continuum, $q_i$ is the heat flux vector, r is the heat source and the source (sink) term of thermal energy, $\sigma_{ij}$ is the stress tensor, and $D_{ij}$ is the deformation rate tensor. Here, the term of double tensor product of $\sigma_{ij} \cdot D_{ij}$ is referred to as a stress power. Further, the summation notation is applied for the subscripts i and j.

Then, when the equation (54) is integrated on the basis of a weighted residual method and then discretized and transformed into a discretized governing equation, the following equation (55) is obtained.

[Expression 55]

$$\frac{\partial \rho_a U_a}{\partial t} + \sum_{b=1}^{m} [\phi_{ab} \cdot \rho \cdot (n_{ab} \cdot u_{ab}) \cdot U_{ab}] = \quad (55)$$

$$-\sum_{b=1}^{m} [\phi_{ab} \cdot (n_{ab} \cdot q_{ab})] + U_a \cdot \rho_a \cdot r_a + U_a \cdot (\sigma : D)_a$$

Then, in addition to the heat flux, the fluxes of all non-mechanical energies such as electric and chemical energies are added up into the heat flux vector [q], the equation for conservation of energy serve as an equation expressing the conservation of energy in a remarkably wide range.

(5) Wave Equation

The above-mentioned equations for physical laws expressed in the conservation form, like the mass conservation equation, the equation for conservation of momentum, the equation for conservation of energy, and the advection diffusion equation, are equations having the properties of both of partial differential equations referred to as a "parabolic type" and an "elliptic type". In contrast, the wave equation expressing the propagation of wave or the propagation of vibration is referred to as a "hyperbolic type", and its general form is shown in the following equation (56).

[Expression 56]

$$\frac{\partial^2 u}{\partial t^2} = \alpha^2 \cdot \left[\frac{\partial^2 u}{\partial x^2} + \frac{\partial^2 u}{\partial y^2} + \frac{\partial^2 u}{\partial z^2}\right] \quad (56)$$

Here, in the equation (56), u is the amplitude or displacement, and $\alpha$ is velocity of propagation of the wave.

Then, when the equation (56) is integrated on the basis of a weighted residual method and then discretized and transformed into a discretized governing equation, the following equation (57) is obtained.

[Expression 57]

$$\frac{\partial^2 u_a}{\partial t^2} = \sum_{b=1}^{m} \left[\phi_{ab} \cdot \alpha^2 \cdot \left(\frac{\partial u}{\partial n}\right)_{ab}\right] \quad (57)$$

As seen from the equation (56), in the direction of space, the discretization technique not requiring the geometric shape of the control volume is directly applicable. Nevertheless, in the time direction, a second order partial derivative is included and hence a precise time integration method is used.

These equations (46), (51), (53), (55), and (57) are equations that are derived on the basis of a weighted residual method and that can calculate physical values by using only values not requiring Vertex and Connectivity. Thus, such equations may be used as a discretized governing equation in the present numerical analysis method.

Then, by using the above-mentioned discretized governing equation, the present numerical analysis method can be applied to numerical analysis for a stationary or non-stationary phenomenon in fluid dynamics, heat conduction, advection diffusion, structural mechanics, wave, or a combination of these.

Next, when the present numerical analysis method is used, the numerical analysis can be performed in a state that components designed in different coordinate systems are built up easily. This is because in the present numerical analysis method, in contrast to the element used in a finite element method, the particular geometric shape of the control volume is not necessary and because the "distance" between two adjacent control points need not be a distance in the absolute coordinate system and may be a "calculative distance".

Thus, according to the present numerical analysis method, as shown in FIG. 13, in a case that numerical analysis is desired to be performed in a state that components A, B, and C designed in different coordinate systems are built up, the numerical analysis can be performed without matching the coordinate systems of these components.

Here, a method for numerical analysis referred to as a general finite element method is a technique that completely inhibits intersection between elements as shown in FIG. 14 or 15. Thus, in application software used in a finite element method, when intersection between elements is detected, an error is outputted. Then, as described above, such situation in a finite element method causes remarkably large work burden in generation of a calculation data model.

On the other hand, according to the present numerical analysis method, as shown in FIG. 14 or 15, intersection is allowed in linkage between control points. This is because informational values such as the volume of the control volume occupied by each control point (the volume of the divided domain), the area of the boundary surface, and the normal vector of the boundary surface need not have a particular geometric shape. Thus, even when linkage between control points intersects, physical value calculation can be executed.

Thus, restriction at the time of generating a calculation data model is reduced. Further, flexibility in generation of a calculation data model is remarkably increased. Nevertheless, in a case that a physical phenomenon in a fluid or the like is to be considered, a property is present that information from control points close to a particular control point updates the physical value of the particular control point. This causes a possibility that when distant control points are linked, calculation precision is degraded. Thus, even in the present numerical analysis method, it is preferable that linkage between control points is formed within an appropriate range.

BRIEF DESCRIPTION OF THE DRAWINGS

FIG. 3 is a table for comparing the present invention with a conventional method for numerical analysis.

FIG. 4 is a diagram for comparing the present invention with a conventional finite volume method in detail.

MODE FOR CARRYING OUT THE INVENTION

With reference to the drawings, described below are a calculation method for physical value, a numerical analysis method, a calculation program for physical value, a numerical analysis program, a calculation device for physical value, and a numerical analysis device according to the present invention.

Here, the following description is given for an embodiment of a numerical analysis method including a calculation method for physical value according to the present invention, a numerical analysis program including a calculation program for physical value according to the present invention, and a numerical analysis device including a calculation device for physical value according to the present invention.

Further, the following embodiment is given for a case that the flow velocity of air in a vehicle cabin space is calculated by numerical analysis.

Figure 1:
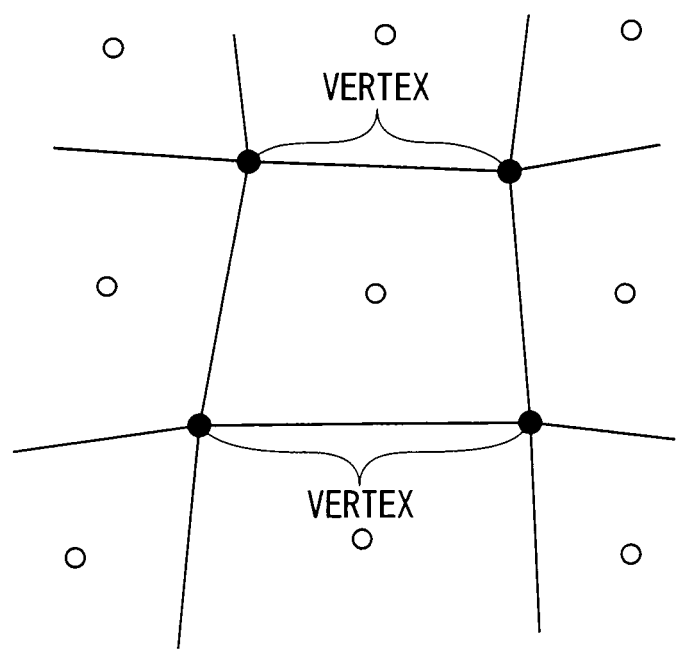
FIG. 1 is a conceptual diagram showing an example of a calculation data model according to a conventional finite element method.
Figure 2:
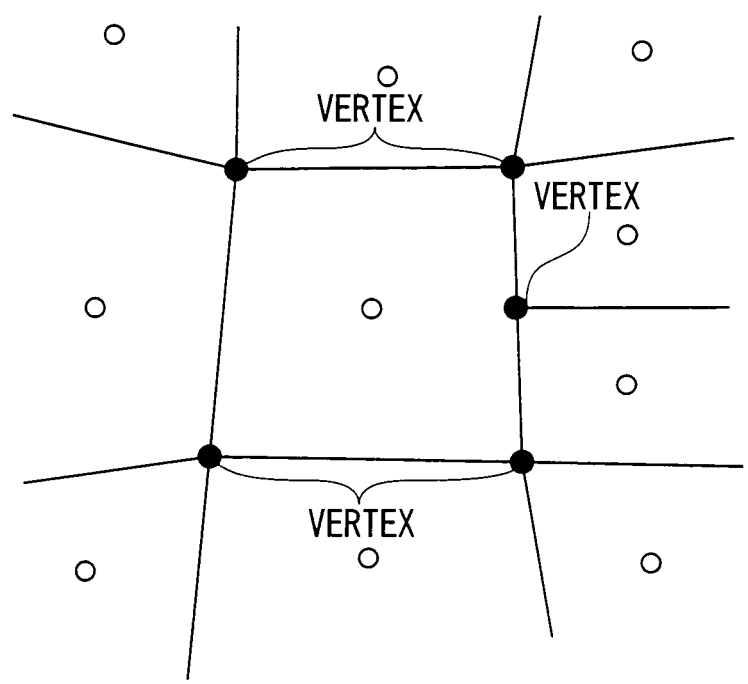
FIG. 2 is a conceptual diagram showing an example of a calculation data model according to a conventional finite volume method.
Figure 5:
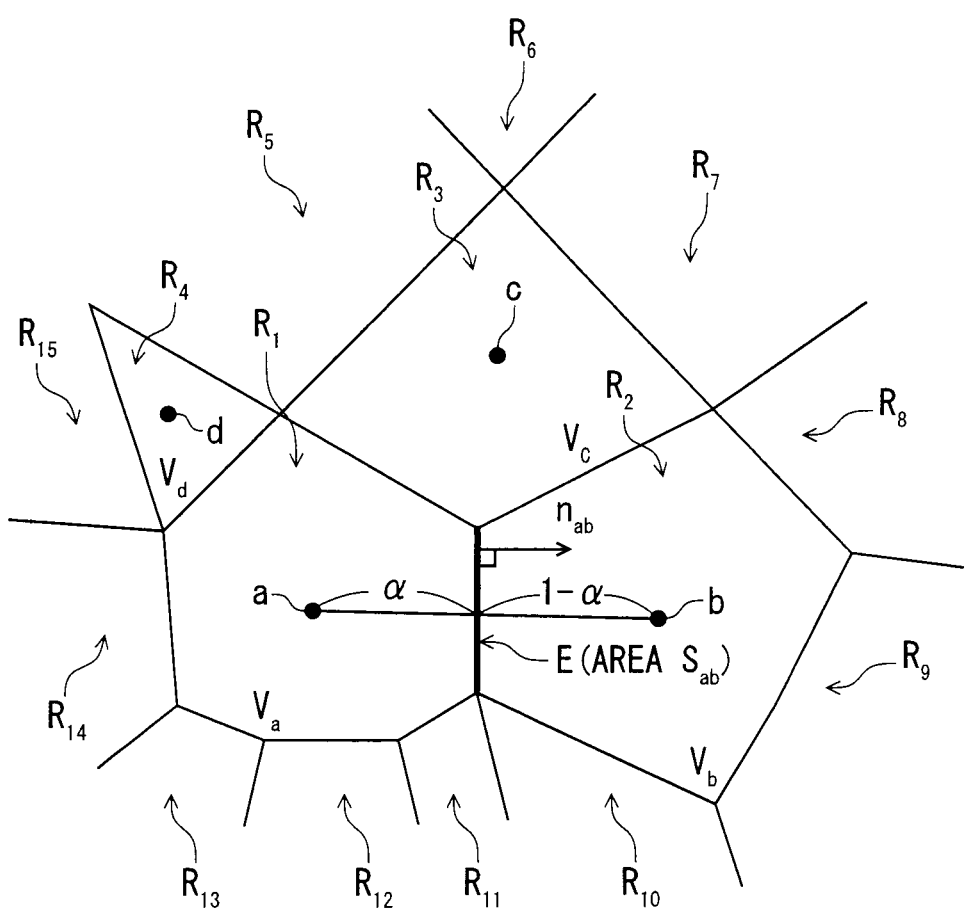
FIG. 5 is a conceptual diagram showing an example of a calculation data model of the present numerical analysis method.
Figure 6:
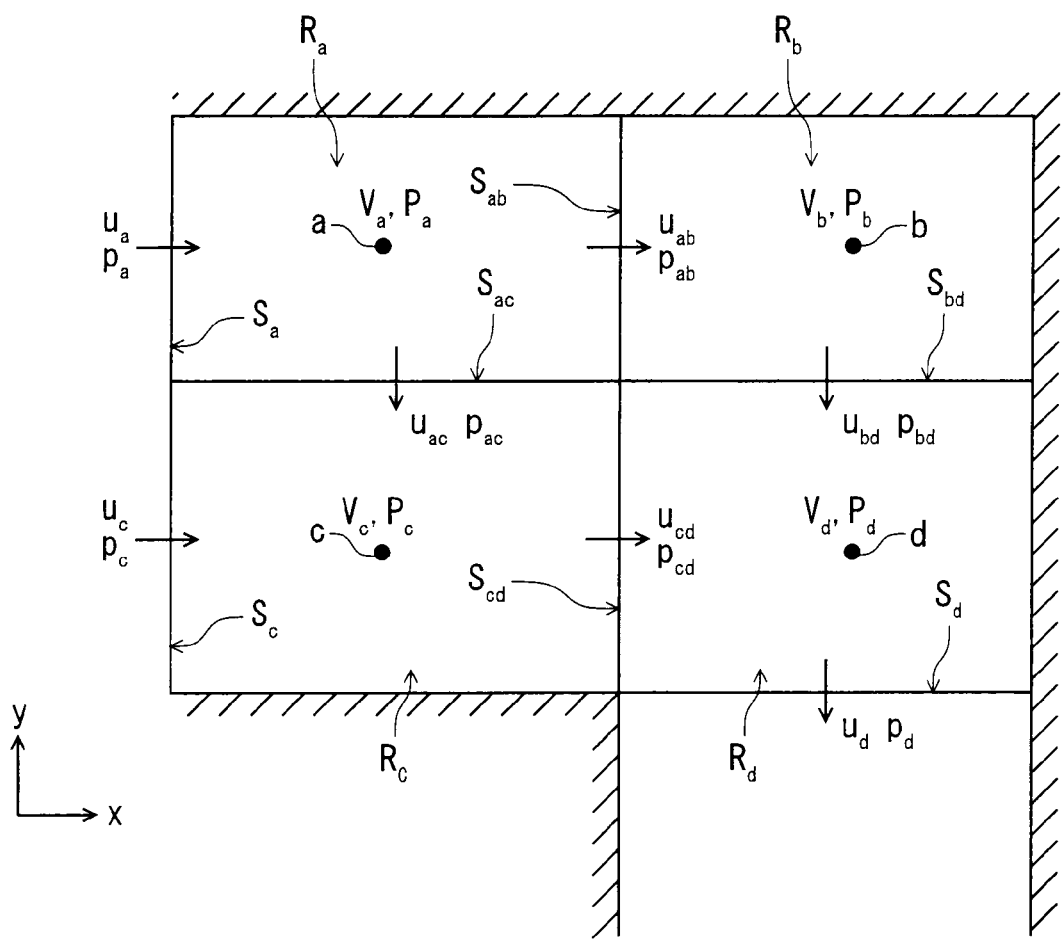
FIG. 6 is a schematic diagram showing a plurality of divided domains for describing a condition necessary for the conservation law for a physical value to be satisfied in the present numerical analysis method.
Figure 7:
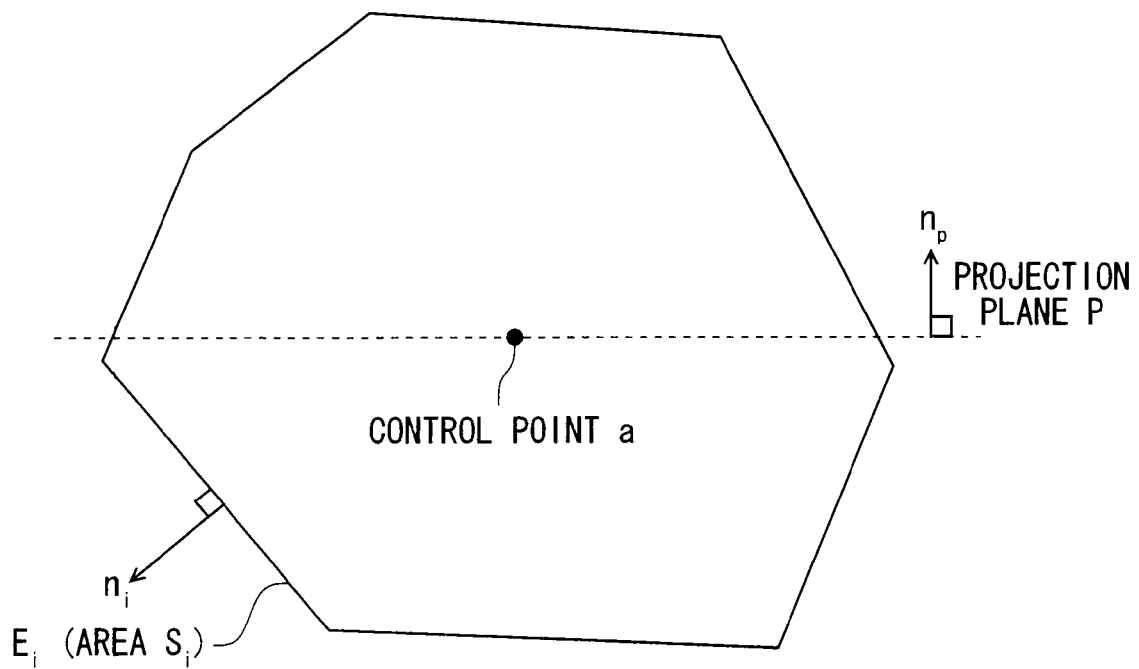
FIG. 7 is a schematic diagram showing an infinitely large projection plane that passes through a control point and that has a unit normal vector in an arbitrary direction.
Figure 8:
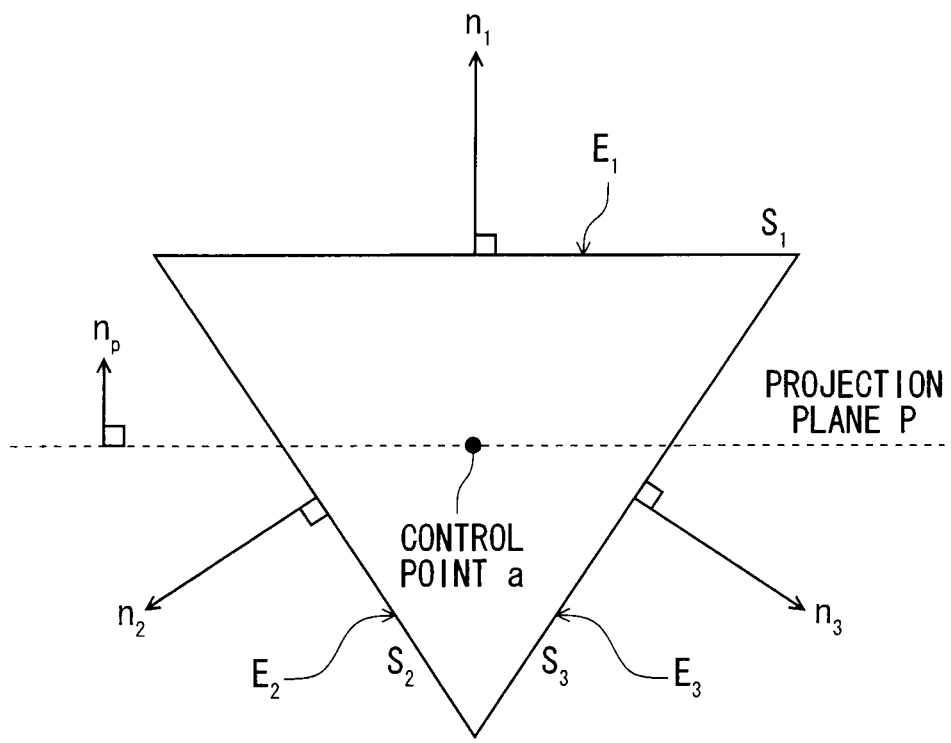
FIG. 8 is a schematic diagram describing a condition necessary for the conservation law for a physical value to be satisfied in a case that a two-dimensional triangular control volume is considered.
Figure 9:
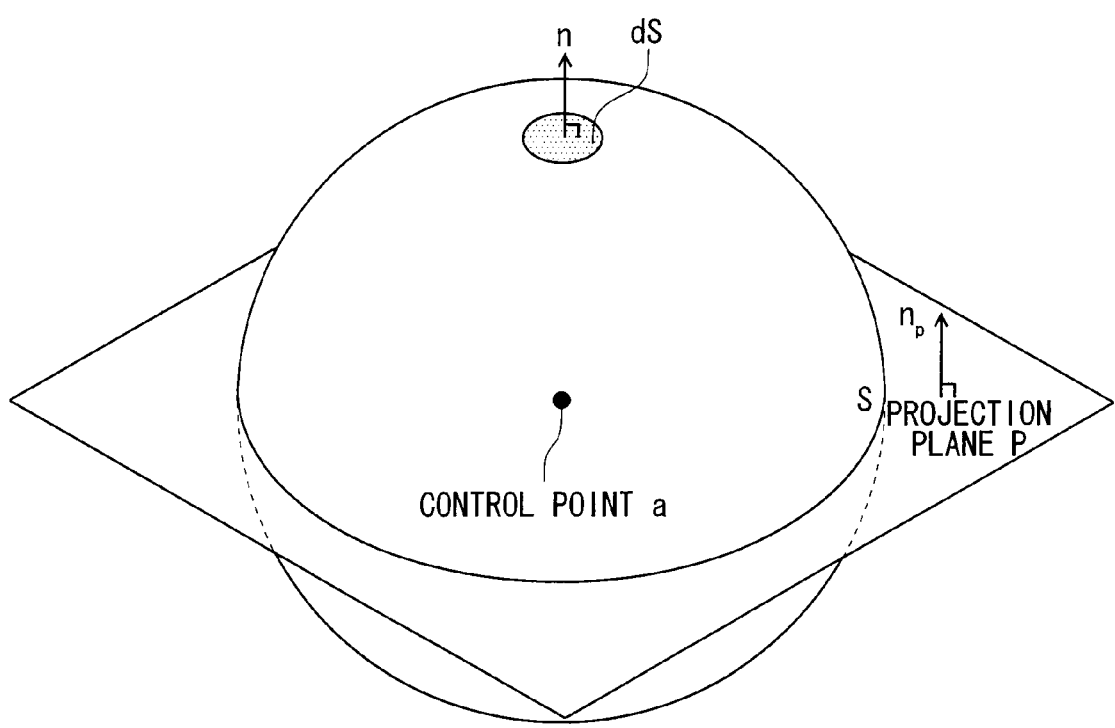
FIG. 9 is a schematic diagram describing a condition necessary for the conservation law for a physical value to be satisfied in a case that a spherical control volume is considered.
Figure 10:
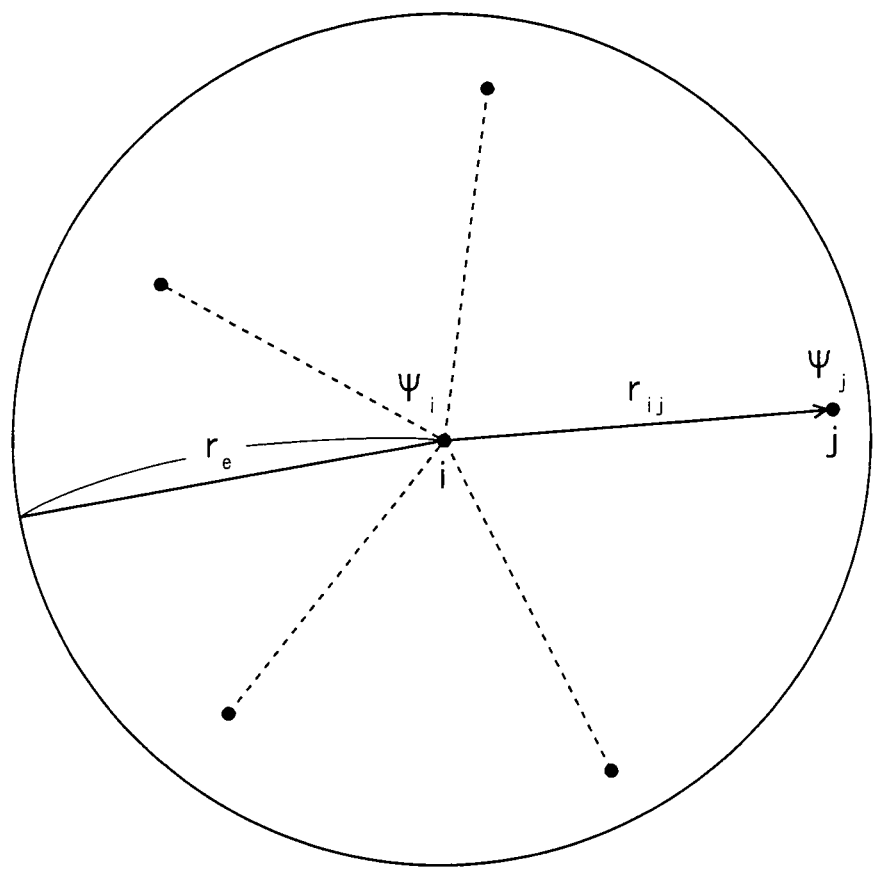
FIG. 10 is a schematic diagram showing neighborhood search in a particle method.
Figure 11:
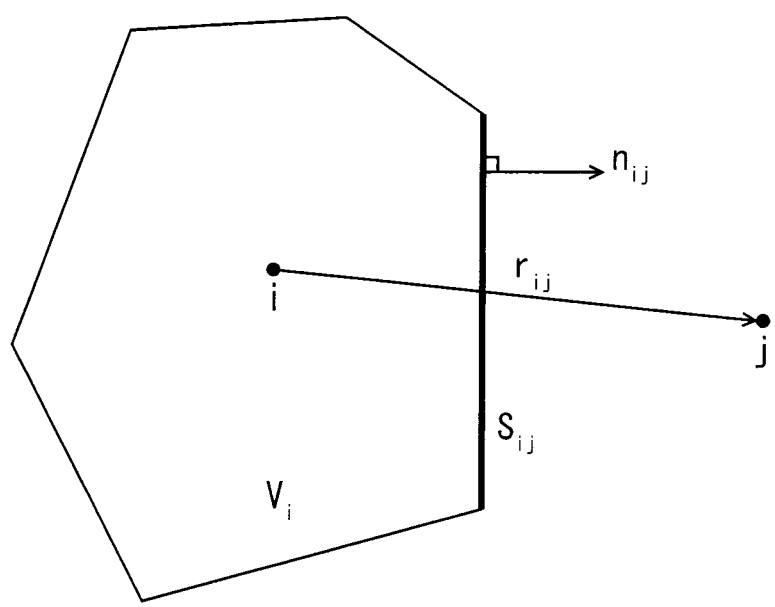
FIG. 11 is a schematic diagram showing a control volume in the present numerical analysis method.
Figure 12:
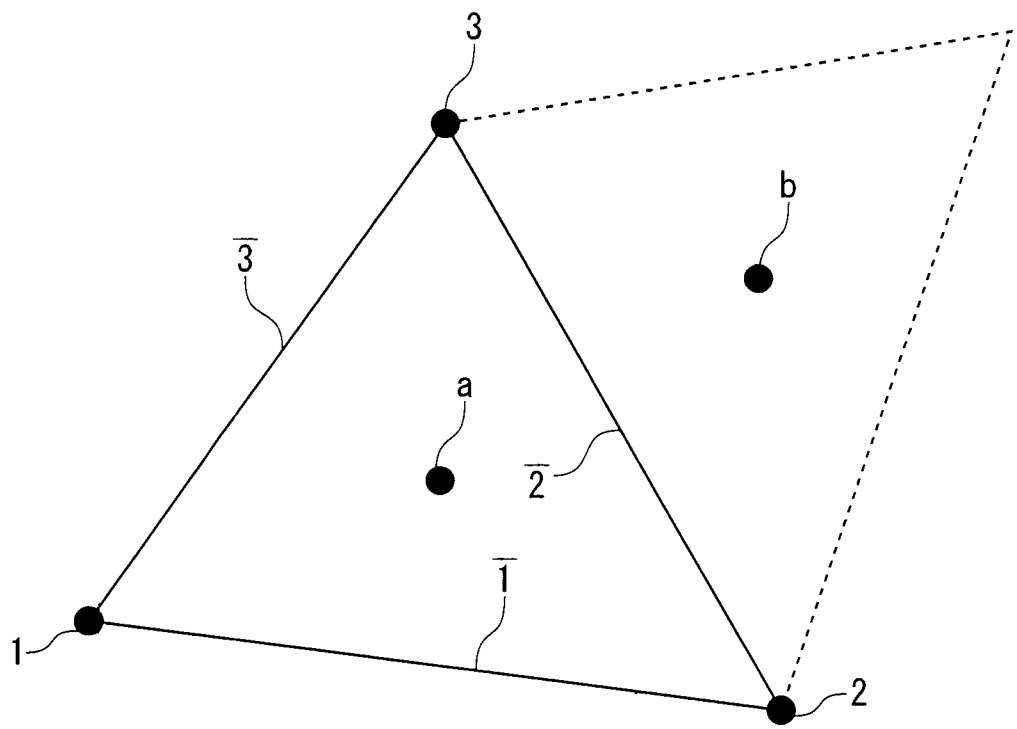
FIG. 12 is a schematic diagram showing a cell having a two-dimensional triangular shape.
Figure 13:
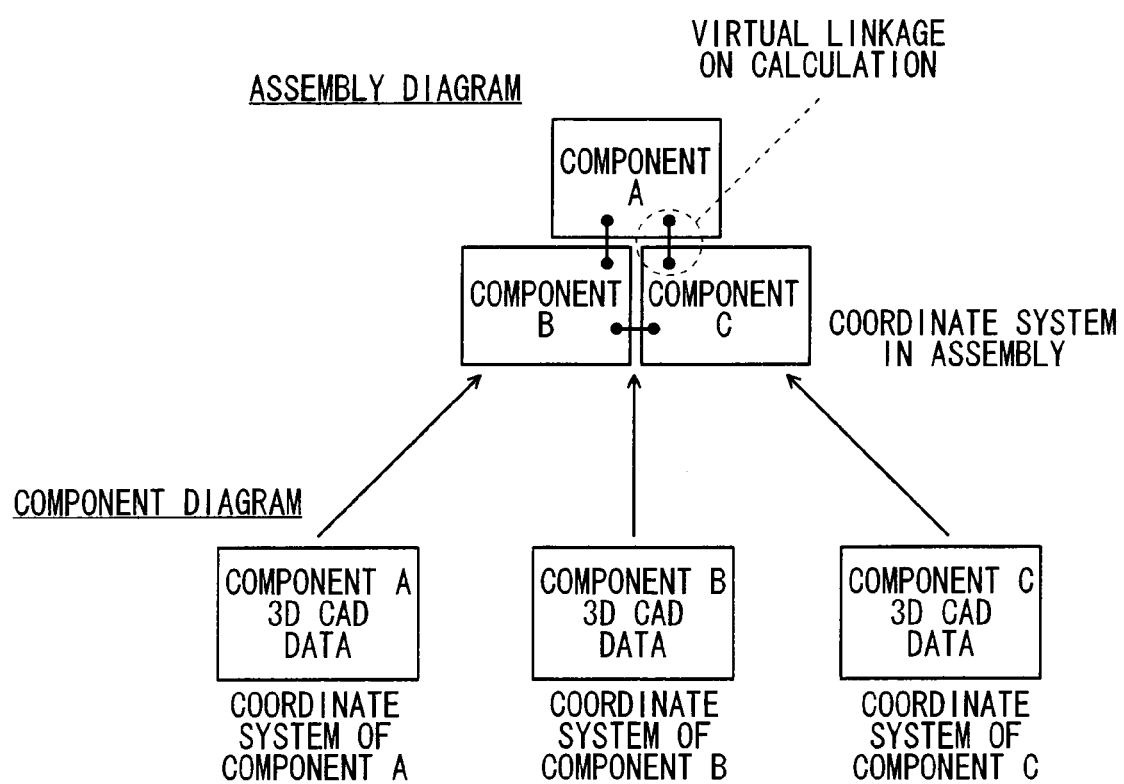
FIG. 13 is a schematic diagram showing a state that components designed in different coordinate systems are built up.
Figure 14:
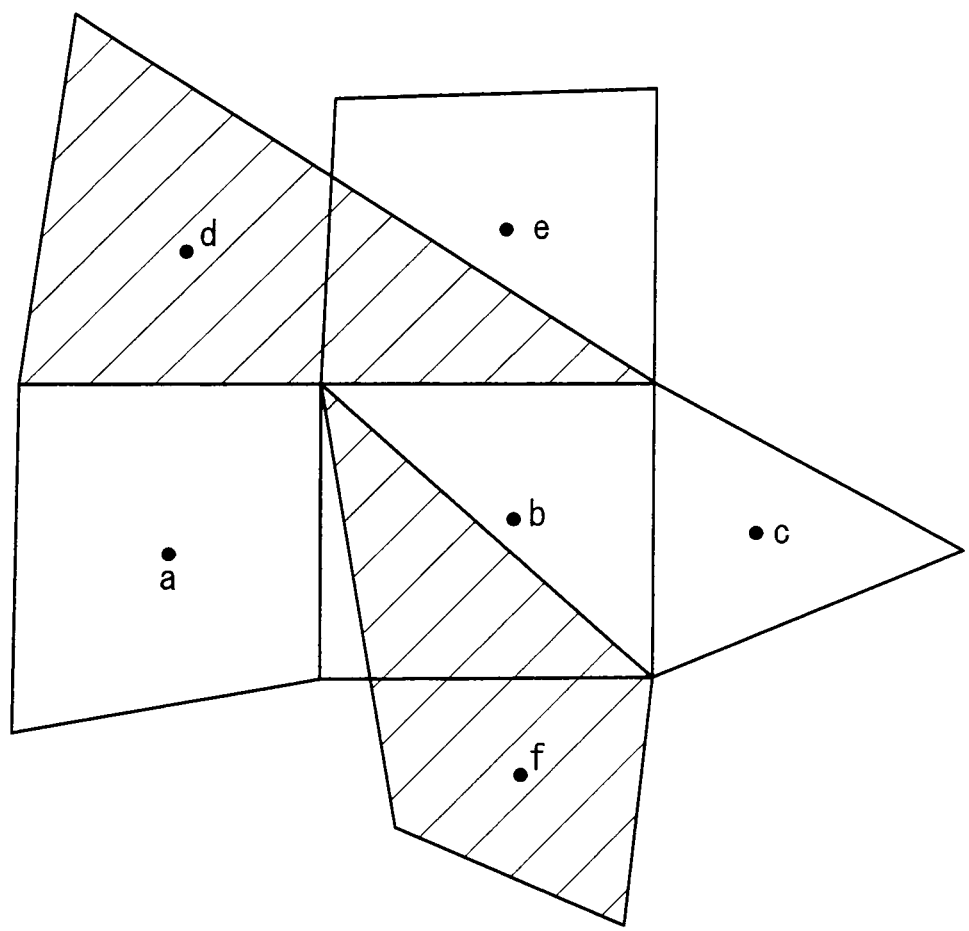
FIG. 14 is a schematic diagram showing a situation that elements intersect with each other.
Figure 15:
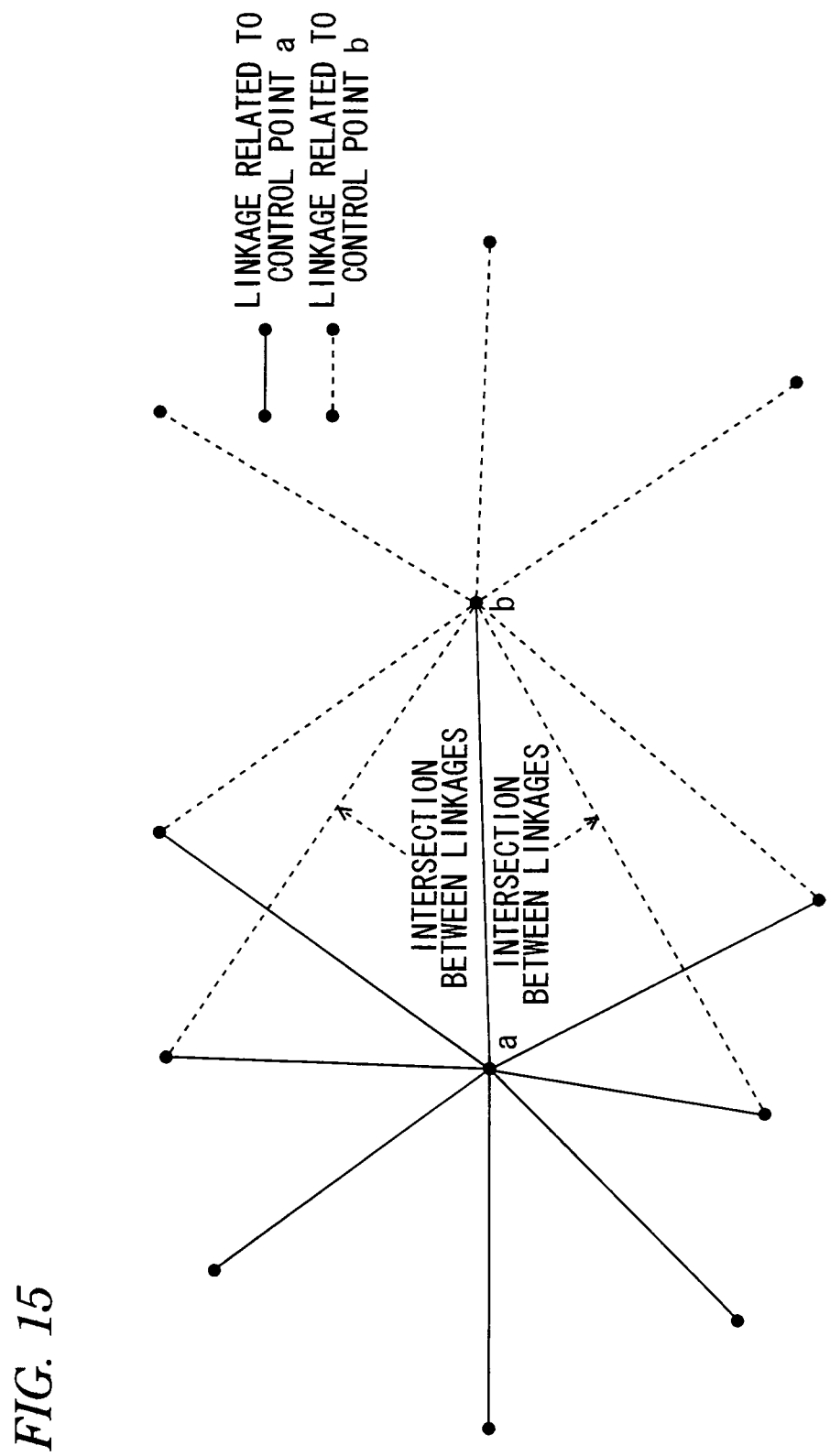
FIG. 15 is a schematic diagram showing a situation that linkages between control points intersect with each other.
Figure 16:
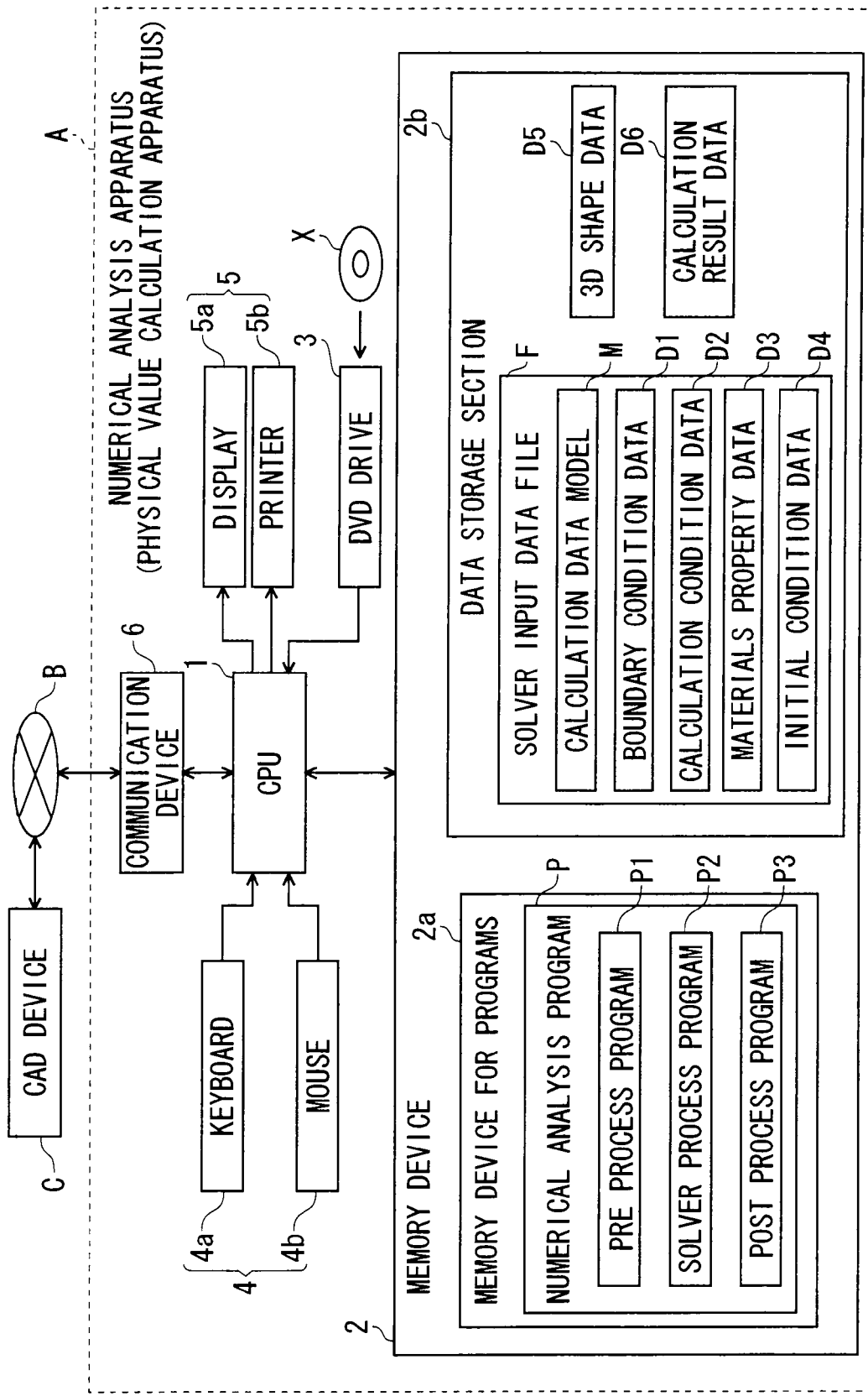
FIG. 16 is a block diagram schematically showing a hardware configuration of a numerical analysis device according to an embodiment of the present invention.

FIG. 16 is a block diagram schematically showing a hardware configuration of a numerical analysis device A according to the present embodiment.

As shown in the figure, the numerical analysis device A according to the present embodiment is constructed from a computer such as a personal computer and a workstation, and has a CPU 1, a memory device 2, a DVD (Digital Versatile Disc) drive 3, an input device 4, an output device 5, and a communication device 6.

The CPU 1 is electrically connected to the memory device 2, the DVD drive 3, the input device 4, the output device 5, and the communication device 6, and processes signals inputted from these various kinds of devices and then outputs the processing results.

The memory device 2 is constructed from an external memory device such as a memory and an internal memory device such as a hard disk drive, and stores information inputted from the CPU 1 and outputs the stored information in response to an instruction inputted from the CPU 1.

Then, the memory device 2 according to the present embodiment has a memory device for programs 2a and a data storage section 2b.

The memory device for programs 2a stores a numerical analysis program P. This numerical analysis program P is an application program executed on a predetermined OS, and causes the numerical analysis device A constructed from a computer according to the present embodiment to perform numerical analysis. Then, the numerical analysis program P causes the numerical analysis device A according to the present embodiment to serve as, for example, calculation data model generating means and physical value calculating means.

Then, as shown in FIG. 16, the numerical analysis program P has a pre process program P1, a solver process program P2, and a post process program P3.

The pre process program P1 causes the numerical analysis device A according to the present embodiment to execute pre process necessary for execution of solver process, and causes the numerical analysis device A according to the present embodiment to serve as calculation data model generating means so as to generate a calculation data model. Further, the pre process program, P1 causes the numerical analysis device A according to the present embodiment to execute setting of conditions necessary for execution of the solver process and further to execute generation of a solver input data file F collecting the calculation data model and the set-up conditions described above.

Then, when causing the numerical analysis device A according to the present embodiment to serve as calculation data model generating means, the pre process program P1 first causes the numerical analysis device A according to the present embodiment to acquire 3D shape data including a vehicle cabin space and then execute generation of an analysis domain expressing the vehicle cabin space included in the acquired 3D shape data.

Here, as described later in detail, the present embodiment, the solver process uses the discretized governing equation described in the above-mentioned method for numerical analysis using the present invention (a discretized governing equation that uses only values not requiring Vertex and Connectivity and that is derived on the basis of a weighted residual method). Thus, at the time of generation of the calculation data model, the shape of the divided domain and the shape of the analysis domain can be changed arbitrarily on condition that the conservation law is satisfied. Thus, the work of correction or change of the vehicle cabin space included in the 3D shape data is achieved by simple lapping or the like. Thus, the pre process program P1 according to the present embodiment causes the numerical analysis device A according to the present embodiment to lap with minute closed surfaces the vehicle cabin space included in the acquired 3D shape data so as to execute lapping for repairing a hole or a gap present in the vehicle cabin space.

After that, the pre process program P1 causes the numerical analysis device A according to the present embodiment to generate divided domains having the same size and execute generation of an analysis domain including the entire domain of the cabin space having undergone the lapping. Then, the pre process program P1 causes the numerical analysis device A according to the present embodiment to cut off domains falling outside the cabin space among the divided domains generated in the same size so as to execute generation of an analysis domain representing the cabin space. Also at this time, since the solver process uses the above-mentioned discretized governing equation, domains falling outside the cabin space in the analysis domain can be cut off easily. This avoids a situation that a boundary to the outer space has a stepwise shape like in a voxel method. Further, in contrast to a cut-cell method of voxel method, generation of an analysis domain near a boundary to the outer space does not require special correction or processing that causes remarkably enormous manual work requiring experience and a trial and error approach. That is, in contrast to a voxel method, the present embodiment does not have a problem associated with the processing for a boundary to the outer space.

Here, in the present embodiment, as described later, a gap between the cabin space and the cut-off domain is filled with divided domains having a new arbitrary shape so that the analysis domain is constructed from divided domains whose shapes are not limited to an orthogonal grid shape. Further, the analysis domain is filled with the divided domains without overlapping.

Further, when causing the numerical analysis device A according to the present embodiment to serve as calculation data model generating means, the pre process program P1 causes the numerical analysis device A according to the present embodiment to execute the processing of virtually arranging one control point in the inside of each divided domain contained in the generated analysis domain representing the cabin space and then store the arrangement information concerning the control points and the volume data concerning the control volume occupied by each control point.

Further, when causing the numerical analysis device A according to the present embodiment to serve as calculation data model generating means, the pre process program P1 causes the numerical analysis device A according to the present embodiment to execute calculation of the area and the normal vector of each boundary surface which is a boundary surface between divided domains described above and then store the area and the normal vector of the boundary surfaces.

Further, when causing the numerical analysis device A according to the present embodiment to serve as calculation data model generating means, the pre process program P1 causes the device to generate the linkage information (Link) concerning the control volumes (control points) and then store the Link.

Then, the pre process program P1 causes the numerical analysis device A according to the present embodiment to collect the volume of the control volume occupied by the above-mentioned individual control point, the area and the normal vector of the boundary surface, the arrangement information (the coordinates) concerning the control points (i.e., divided domains) and the Link, and then generate a calculation data model.

Further, when causing the numerical analysis device A according to the present embodiment to execute setting of conditions necessary for execution of the above-mentioned solver process, the pre process program P1 causes the device to perform setting of property, setting of boundary conditions, setting of initial conditions, and setting of calculation conditions.

Here, the materials property values indicate the density, the coefficient of viscosity, and the like of air in the cabin space.

The boundary conditions set forth rules used at the time of exchange of a physical value between control points and are, in the present embodiment, a discretized governing equation based on the Navier-Stokes equations shown in the equation (10) given above and a discretized governing equation based on the continuity equation shown in the equation (11).

Further, the boundary conditions include information specifying divided domains facing a boundary surface between the cabin space and the outer space.

The initial conditions specify physical values in the beginning of execution of the solver process, and are initial values for the flow velocity of each divided domain.

The calculation conditions are conditions concerning the calculation in the solver process and are, for example, the number of iteration and a criterion for convergence.

Further, the pre process program P1 causes the numerical analysis device A according to the present embodiment to form a GUI (Graphical User Interface). More specifically, the pre process program P1 causes the display 5a provided in the output device 5 to display graphics, and generates a state that operation is allowed through the keyboard 4a and the mouse 4b provided in the input device 4.

The solver process program P2 (a calculation program for physical value) causes the numerical analysis device A according to the present embodiment to execute solver process, and causes the numerical analysis device A according to the present embodiment to serve as a calculation device for physical value.

Then, when causing the numerical analysis device A according to the present embodiment to serve as physical value calculating means, the solver process program P2 causes the device to perform physical value calculation on the physical values in the analysis domain by using the solver input data file F containing the volume of the control volume, the area of the boundary surface, and the normal vector provided in the calculation data model.

Then, when causing the numerical analysis device A according to the present embodiment to serve as physical value calculating means, the solver process program P2 causes the numerical analysis device A according to the present embodiment to execute generation of a discretization coefficient matrix for the Navier-Stokes equations and the continuity equation contained in the solver input data file F and then execute generation of a data table for matrix generation.

Further, when causing the numerical analysis device A according to the present embodiment to serve as physical value calculating means, the solver process program P2 causes the numerical analysis device A according to the present embodiment to execute build-up of a large sparse matrix equation for matrix calculation shown in the following equation (58), by using the discretized governing equation based on the Navier-Stokes equations shown in the equation (10) described above and the discretized governing equation based on the continuity equation shown in the equation (11) described above.

[Expression 58]

$$A \cdot X = B \quad (58)$$

Here, in the equation (58), [A] denotes a large sparse matrix, [B] denotes a boundary condition vector, and [X] denotes a solution.

Further, when an additional condition such as incompressibility is present in the above-mentioned discretized governing equation, the solver process program P2 causes the numerical analysis device A according to the present embodiment to execute incorporation of the additional condition into the matrix equation.

Then, the solver process program P2 causes the numerical analysis device A according to the present embodiment to execute calculation of the solution of the matrix equation by a CG method (conjugate gradient method) or the like, update of the solution by using the following equation (59), and judgment of the convergence condition, and thereby to acquire a final calculation result.

[Expression 59]

$$A(X^n) \cdot X^{n+1} = B(X^n) \quad (59)$$

The post process program P3 causes the numerical analysis device A according to the present embodiment to execute post process, and causes the numerical analysis device A according to the present embodiment to execute processing based on the calculation result acquired in the solver process.

More specifically, the post process program P3 causes the numerical analysis device A according to the present embodiment to execute visualization process and extraction processing for the calculation result.

Here, the visualization process is, for example, the processing of causing the output device 5 to output a display of contour of cross section, a vector display, an equi-contour surface display, and an animation display. Further, the extraction processing is the processing of causing the output device 5 to extract quantitative values in the domain specified by an operator and then output them as numerical values or a graph or alternatively to extract the quantitative values in the domain specified by the operator and then output them in the form of a file.

Further, the post process program P3 causes the numerical analysis device A according to the present embodiment to execute automatic report generation, calculation residual display, and analysis.

As shown in FIG. 16, the data storage section 2b stores: a solver input data file F containing a calculation data model M, data of boundary conditions D1 describing the boundary conditions, calculation condition data D2 describing the calculation conditions, materials property data D3 describing the materials property values, and initial condition data D4 describing initial conditions; 3D shape data D5; calculation result data D6; and the like. Further, the data storage section 2b temporarily stores intermediate data generated in the course of processing by the CPU 1.

The DVD drive 3 is constructed such that a DVD medium X can be inserted therein. Then, in response to an instruction inputted from the CPU 1, the DVD drive outputs the data stored in the DVD medium X. In the present embodiment, the numerical analysis program P is stored in the DVD medium X. Then, in response to an instruction inputted from the CPU 1, the DVD drive 3 outputs the numerical analysis program P stored in the DVD medium X.

The input device 4 is a man-machine interface between the numerical analysis device A according to the present embodiment and an operator, and has a keyboard 4a and a mouse 4b serving as pointing devices.

The output device 5 outputs in a visualized manner a signal inputted from the CPU 1, and has a display 5a and a printer 5b.

The communication device 6 performs data transfer between the numerical analysis device A according to the present embodiment and an external device such as a CAD device C, and is electrically connected to a network B such as an intra-company LAN (Local Area Network).

Next, a numerical analysis method using the numerical analysis device A having the above-mentioned configuration according to the present embodiment (a numerical analysis method according to the present embodiment) is described below with reference to the flow chart of FIGS. 17 to 19.

Figure 17:
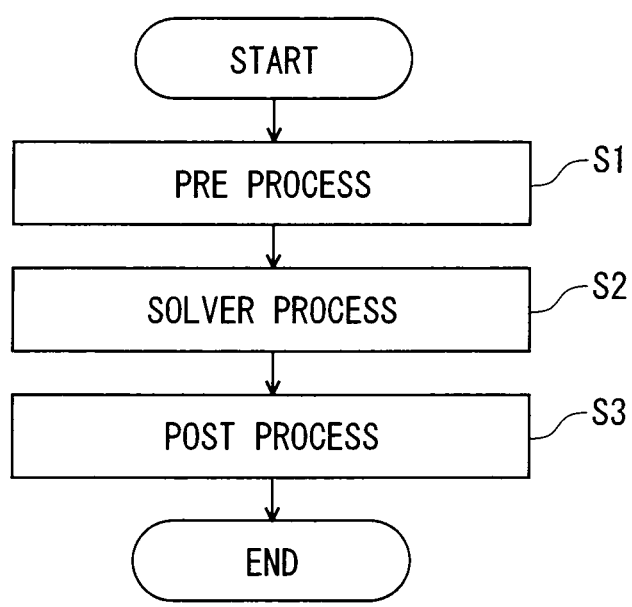
FIG. 17 is a flow chart showing a numerical analysis method according to an embodiment of the present invention.

As shown in the flow chart of FIG. 17, the numerical analysis method according to the present embodiment is constructed from pre process (step S1), solver process (step S2), and post process (step S3).

Here, before performing the numerical analysis method according to the present embodiment, the CPU 1 extracts from the DVD medium X the numerical analysis program P stored in the DVD medium X inserted into the DVD drive 3, and then stores the program into the memory device for programs 2a of the memory device 2.

Then, when a signal instructing the start of numerical analysis is inputted through the input device 4, the CPU 1 executes numerical analysis on the basis of the numerical analysis program P stored the memory device 2. More specifically, the CPU 1 executes pre process (step S1) on the basis of the pre process program P1 stored in the memory device for programs 2a, then executes solver process (step S2) on the basis of the solver process program P2 stored in the memory device for programs 2a, and then executes cost process (step S3) on the basis of the post process program P3 stored in the memory device for programs 2a. As such, when the CPU 1 executes the pre process (step S1) on the basis of the pre process program P1, the numerical analysis device A according to the present embodiment serves as calculation data model generating means. Further, when the CPU 1 executes the solver process (step S2) on the basis of the solver process program P2, the numerical analysis device A according to the present embodiment serves as physical value calculating means.

Figure 18:
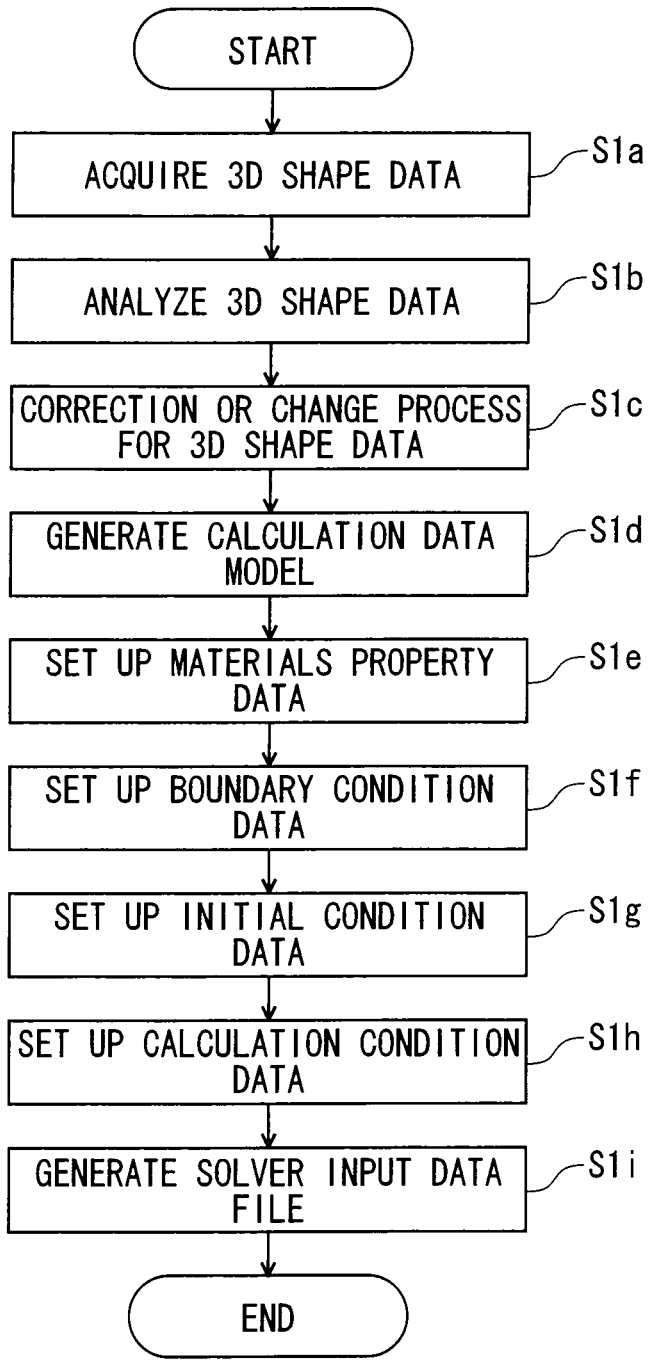
FIG. 18 is a flow chart showing pre process performed in a numerical analysis method according to an embodiment of the present invention.

FIG. 18 is a flow chart showing the pre process (step S1). As shown in the figure, when the pre process (step S1) is started, the CPU 1 causes the communication device 6 to acquire the 3D shape data D5 including the vehicle cabin space, from the CAD device C via the network B (step S1a). The CPU 1 stores the acquired 3D shape data D5 into the data storage section 2b of the memory device 2.

Then, the CPU 1 performs analysis of the 3D shape data D5 acquired at step S1a (step S1b) so as to detect mutually overlapping curved surfaces, mutually intersecting curved surfaces, a gap between curved surfaces, a small hole, and the like contained in the 3D shape data D5 stored in the data storage section 2b.

Then, the CPU 1 executes correction or change processing for the 3D shape data D5 acquired at step S1a (step S1c).

Figure 20:
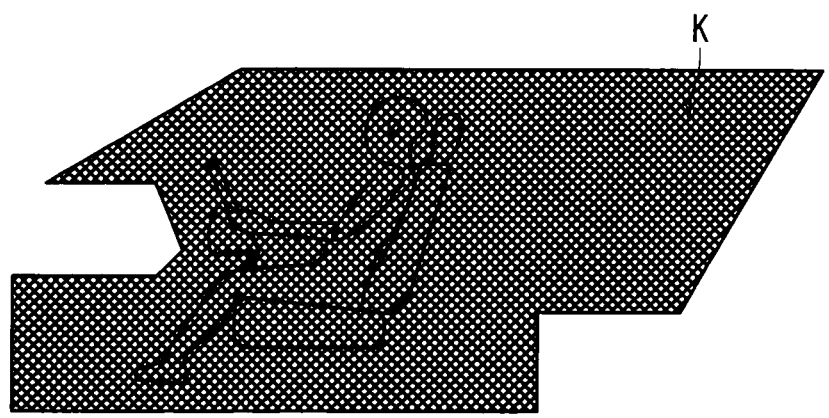
FIG. 20 is a schematic diagram showing a situation that a vehicle cabin space contained in 3D shape data is lapped by minute closed surfaces.

More specifically, as shown in FIG. 20, the CPU 1 performs lapping by using minute closed surfaces onto the cabin space K included in the 3D shape data D5, so as to correct the 3D shape data D5 for the cabin space such that mutually overlapping curved surfaces, mutually intersecting curved surfaces, a gap between curved surfaces, a small hole, and the like are eliminated.

Here, in the correction or change processing (step S1c), the CPU 1 generates a GUI. Then, when an instruction (e.g., an instruction specifying a lapping domain) is inputted through the GUI, the CPU executes correction or change processing where the instruction is reflected.

Then, the CPU 1 executes the generation of the calculation data model (step S1d).

Figure 21:
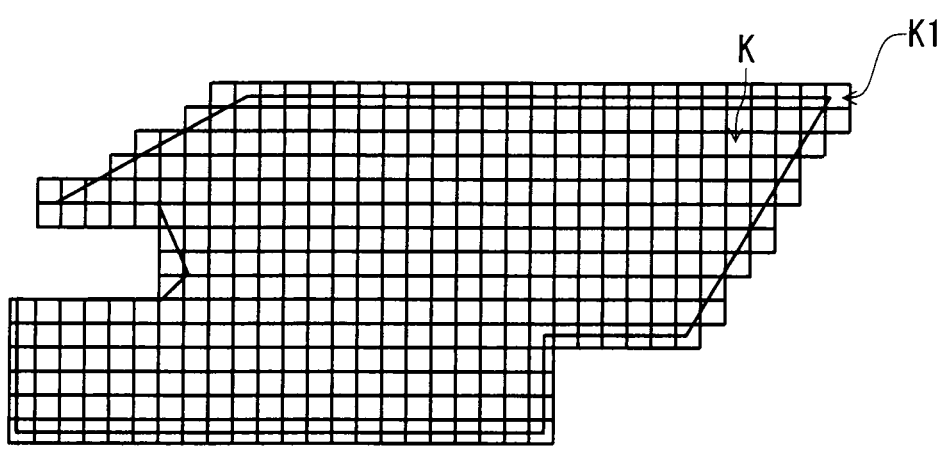
FIG. 21 is a schematic diagram showing a situation that an analysis domain including a vehicle cabin space contained in 3D shape data is formed by divided domains having the same orthogonal grid shape.

More specifically, as shown in FIG. 21, on the basis of the 3D shape data D5 corrected or changed at step S1c, the CPU 1 first executes generation of an analysis domain K1 that includes the entire domain of the cabin space and that is divided uniformly with divided domains having the same shape (an orthogonal grid). Here, it is assumed that the analysis domain K1 is divided with divided domains having the same shape for the purpose of shortening the time. However, the divided domains constituting the analysis domain K1 need not have the same shapes and may have arbitrary shapes.

Figure 22:
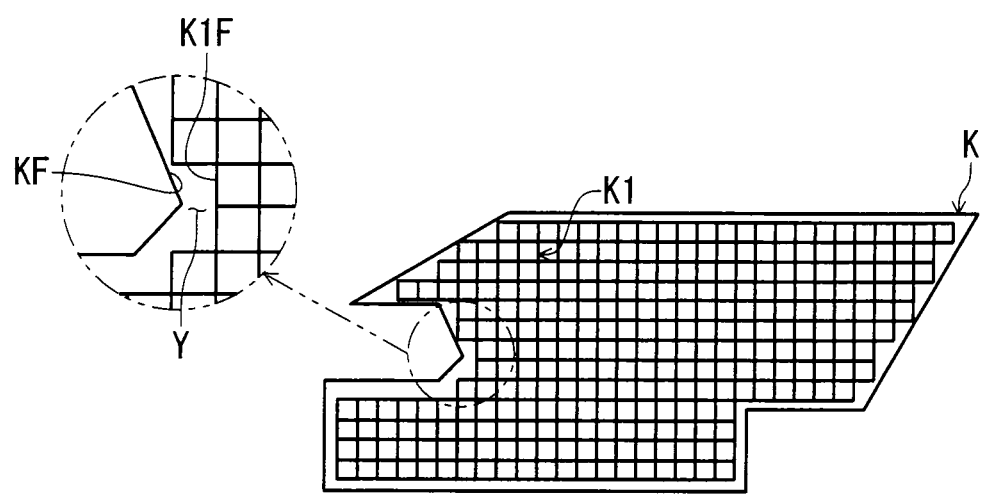
FIG. 22 is a schematic diagram showing a situation that divided domains falling outside a cabin space have been deleted.

Then, as shown in FIG. 22, the CPU 1 deletes divided domains falling outside the cabin space K so that the analysis domain K is accommodated inside the cabin space K without falling outside. As a result, as shown in the enlarged view of FIG. 22, a gap Y is formed between a boundary surface K1F of the analysis domain K1 and a boundary surface KF of the cabin space K.

Figure 23:
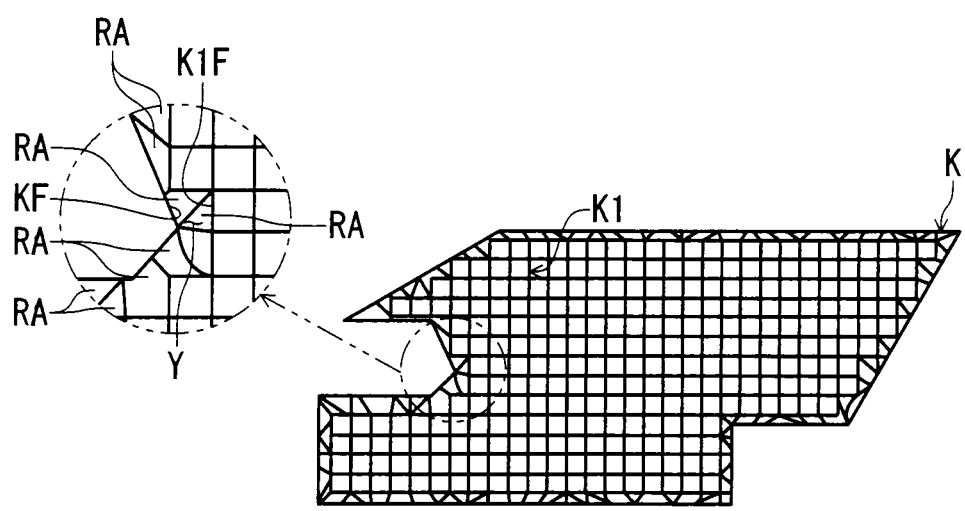
FIG. 23 is a schematic diagram showing a situation that a gap formed between a boundary surface of an analysis domain and a boundary surface of a cabin space is filled with new divided domains.

Then, as shown in FIG. 23, the CPU 1 fills the gap Y with new divided domains RA that constitute a part of the analysis domain.

As described above in detail in the explanation of the principle, in the numerical analysis method according to the present embodiment, a calculation data model not having Vertex and Connectivity is generated. Then, the calculation data model generation can be performed without restriction on the geometric shape of each divided domain. That is, at the time of generation of a calculation data model, the divided domains constituting the analysis domain K1 may have arbitrary shapes. Thus, at the time of filling the gap Y with new divided domains RA, the CPU 1 may arbitrarily set up the shapes of the divided domains RA as shown in the enlarged view of FIG. 23. Thus, filling of the gap Y with the divided domains RA is achieved remarkably easily. For example, in place of a configuration that an operator performs the work through the GUI, automatic generation of the divided domains RA is sufficiently achievable. If the gap Y were tentatively to be filled with divided domains in a conventional finite volume method, as described above, the divided domains need be arranged such that deformation or twist should not arise in accordance with the restriction on the geometric shape of the divided domain. This work is an operator's manual work, and hence causes enormous load to the operator and an increase in the analysis time.

Then, the CPU 1 virtually arranges one control point in the inside of each divided domain included in the analysis domain representing the cabin space. Here, the CPU 1 calculates the centroid of the divided domain and then virtually arranges one control point to each centroid. Then, the CPU 1 calculates the arrangement information concerning the control points and the volume of the control volume occupied by each control point (the volume of the divided domain where the control point is arranged) and then temporarily stores these into the data storage section 2b of the memory device 2.

Further, the CPU 1 calculates the area and the normal vector of each boundary surface which is a boundary surface between divided domains, and then temporarily stores the areas and the normal vectors of these boundary surfaces into the data storage section 2b of the memory device 2.

Further, the CPU 1 generates Link and then temporarily stores the Link into the data storage section 2b of the memory device 2.

Then, the CPU 1 brings into the form of a database the arrangement information concerning the control points, the volume of the control volume occupied by each control point, the area and the normal vector of each boundary surface, and the Link which have been stored in the data storage section 2b, so as to generate a calculation data model M and then store the generated calculation data model into the data storage section 2b of storage section 2.

Here, at such a step S1d, the analysis domain including the cabin space is divided uniformly into divided domains having the same shape, then divided domains falling outside the cabin space are deleted, and then a gap having occurred between the analysis domain and the cabin space is filled with new divided domains so that a final analysis domain K2 is generated. Thus, a state is realized that the entire domain of the cabin space is filled with divided domains without overlapping.

Thus, the calculation data model satisfies the above-mentioned three conditions (a) to (c) necessary for satisfying the conservation law.

Further, in the present embodiment, at step S1d, a configuration is employed that divided domains are generated first, then control points are arranged, and then a volume of the divided domain is assigned to each control point.

However, in the present invention, control points may first be arranged to the analysis domain, and then a volume may be assigned to each control point.

Specifically, for example, a weight is imparted to each control point on the basis of the radius causing collision with other control point or alternatively on the basis of the distance to a control point in linkage relation (related by Link).

Here, the weight of the control point i is $w_i$, the reference volume is $V^+$, and the volume $V_i$ assigned to the control point i is as shown in the following equation (60).

[Expression 60]

$$V_i = w_i \cdot V^+ \quad (60)$$

Further, the total sum of the volumes $V_i$ of the individual control points is equal to the volume $V_{total}$ of the analysis domain. Thus, the following equation (61) holds.

[Expression 61]

$$\sum_i V_i = V^+ \cdot \sum_i w_i = V_{total} \quad (61)$$

As a result, the reference volume $V^+$ is obtained from the following equation (62).

[Expression 62]

$$V^+ = V_{total} / \sum_i w_i \quad (62)$$

Thus, the volume to be assigned to each control point is obtained from the equations (61) and (62).

According to this method, in the pre process, the volumes of divided domains to be provided in the calculation data model are obtained without using Vertex and Connectivity.

Further, in the generation of the calculation data model (step S1d), the CPU 1 generates a GUI. Then, when an instruction (i.e., an instruction specifying the density of the divided domain or an instruction specifying the shape of the divided domain) is inputted through the GUI, the CPU executes processing in which the instruction is reflected. Thus, by operating the GUI, an operator can arbitrarily adjust the arrangement of the control points and the shapes of the divided domains.

However, the CPU 1 checks satisfaction of the three conditions necessary for satisfying the conservation law which is stored in the numerical analysis program. Then, when the instruction inputted through the GUI violates the conditions, the CPU displays the situation on the display 5a.

Then, the CPU 1 performs setting of the materials property data (step S1e). Specifically, the CPU 1 displays an input screen for materials property values onto the display 5a through the GUI. Then, signals indicating materials property values inputted through the keyboard 4a or the mouse 4b are temporarily stored as the materials property data D3 into the data storage section 2b, so that the materials property values are set up. Here, the materials property values mentioned here indicate the characteristic values of the fluid (i.e., air) in the cabin space, like the density, the coefficient of viscosity, and the like of air.

Then, the CPU 1 performs setting of the data of boundary conditions (step S1f). Specifically, the CPU 1 displays an input screen for boundary conditions onto the display 5a through the GUI. Then, signals indicating boundary conditions inputted through the keyboard 4a or the mouse 4b are temporarily stored as the data of boundary conditions D1 into the data storage section 2b, so that the data of boundary conditions is set up. Here, the boundary conditions mentioned here indicate: a discretized governing equation that governs the physical phenomenon in the cabin space; information that specifies control points facing the boundary surface between the cabin space and the outer space; the conditions for heat conduction of heat between the cabin space and the outer space; and the like.

Here, in the numerical analysis method according to the present embodiment, its object is to obtain the flow velocity in the cabin space by numerical analysis. Thus, the above-mentioned discretized governing equations are the discretized governing equation (10) based on the above-mentioned Navier-Stokes equations and the discretized governing equation (11) based on the continuity equation.

Here, these discretized governing equations are selected, for example, by a method that a plurality of discretized governing equations stored in advance in the numerical analysis program P are displayed on the display 5a and then an operator selects any one or ones from the displayed plurality of discretized governing equations by using the keyboard 4a and the mouse 4b.

Then, the CPU 1 performs setting of the initial condition data (step S1g). Specifically, the CPU 1 displays an input screen for initial conditions onto the display 5a through the GUI. Then, signals indicating initial conditions inputted through the keyboard 4a or the mouse 4b are temporarily stored as the initial condition data D4 into the data storage section 2b, so that the initial condition data is set up. Here, the initial condition mentioned here indicates the initial flow velocity at each control point (each divided domain).

Then, the CPU 1 performs setting of the calculation condition data (step S1h). Specifically, the CPU 1 displays an input screen for calculation conditions onto the display 5a through the GUI. Then, signals indicating calculation conditions inputted through the keyboard 4a or the mouse 4b are temporarily stored as the calculation condition data D2 into the data storage section 2b, so that the calculation condition data is set up. Here, the calculation conditions mentioned here indicate conditions for the calculation in the solver process (step S2), like the number of iteration and criterion for convergence.

Then, the CPU 1 performs generation of a solver input data file F (step S1i).

Specifically, the CPU 1 stores in the solver input data file F the calculation data model M generated at step S1d, the materials property data D3 set up at step S1e, the data of boundary conditions D1 set up at step S1f, the initial condition data D4 set up at step S1g, and the calculation condition data D2 set up at step S1h, and thereby generates the solver input data file F. Here, the solver input data file F is stored into the data storage section 2b.

Figure 19:
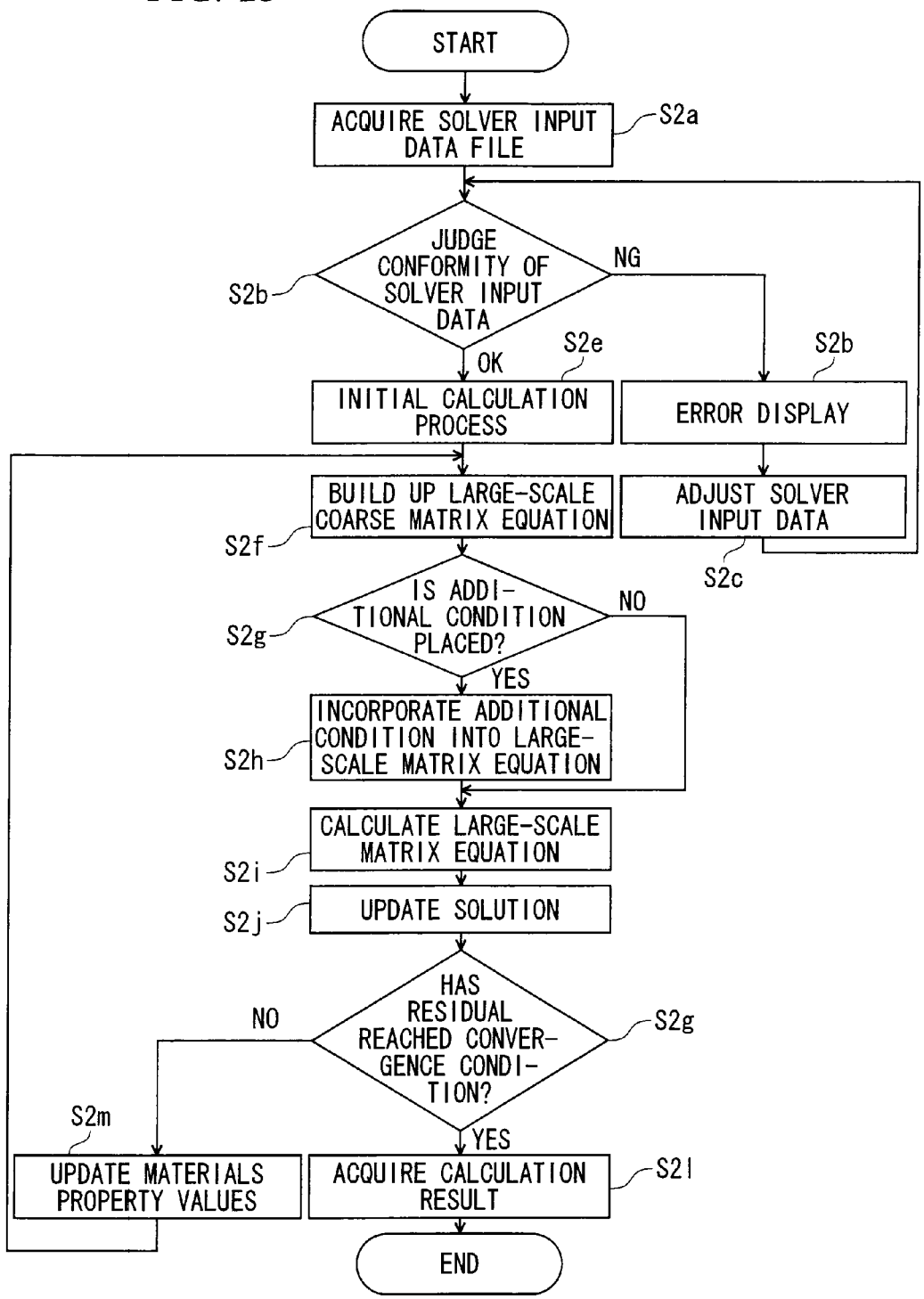
FIG. 19 is a flow chart showing solver process performed in a numerical analysis method according to an embodiment of the present invention.

When the pre process (step S1) as described here is completed, the CPU 1 executes the solver process (step S2) shown in the flow chart of FIG. 19 on the basis of the solver process program P2.

As shown in FIG. 19, when the solver process (step S2) is started, the CPU 1 acquires the solver input data file F generated in the pre process (step S1) (step S2a). Here, in a case that the pre process and the solver process are executed by a single device (the numerical analysis device A according to the present embodiment) like in the numerical analysis method according to the present embodiment, the solver input data file F is already stored in the data storage section 2b. Thus, this step S2a may be skipped. Nevertheless, in a case that the pre process (step S1) and the solver process (steps S2) are executed by mutually different devices, the solver input data file F conveyed through a network or a removable disk need be acquired and hence the present step S2a need be executed.

Then, the CPU 1 judges the conformity of the solver input data (step S2b). Here, the solver input data is data stored in the solver input data file F, and includes the calculation data model M, the data of boundary conditions D1, the calculation condition data D2, the materials property data D3, and the initial condition data D4.

Specifically, the CPU 1 analyzes whether all kinds of solver input data necessary for the execution of physical value calculation in the solver process are stored in the solver input data file F, and thereby judges the conformity of the solver input data.

Then, when it is judged that the solver input data is of inconformity, the CPU 1 displays an error on the display 5a (step S2b), and then displays a screen through which data of the inconformity part is inputted. After that, on the basis of a signal inputted through the GUI, the CPU 1 performs adjustment of the solver input data (step S2c), and then executes step S2a again.

On the other hand, when it is judged at step S2b that the solver input data has conformity, the CPU 1 executes initial calculation (step S2e).

Specifically, the CPU 1 generates a discretization coefficient matrix from the discretized governing equations (i.e., the discretized governing equation (10) based on the Navier-Stokes equations and the discretized governing equation (11) based on the continuity equation) stored in the data of boundary conditions D1, and then generates a data table for matrix calculation so as to perform the initial calculation.

Then, the CPU 1 performs build-up of a large sparse matrix equation (step S2f). Specifically, by using the discretized governing equation (10) based on the Navier-Stokes equations and the discretized governing equation (11) based on the continuity equation, the CPU 1 performs build-up of the large sparse matrix equation for matrix calculation shown in the above-mentioned equation (58).

Then, the CPU 1 judges whether an additional condition such as incompressibility and contact is placed on the discretized governing equation. Such an additional condition is, for example, stored as data of boundary conditions in the solver input data file F.

Then, when it is judged that an additional condition is placed on the discretized governing equation, the CPU 1 executes build-in of the additional condition into the large matrix equation (step S2h), and then executes calculation of the large matrix equation (step S2i). In contrast, when it is judged that no additional condition is placed on the discretized governing equation, the CPU 1 does not execute build-in of an additional condition into the large matrix equation (step S2h), and then executes calculation of the large matrix equation (step S2i).

Then, the CPU 1 solves the large matrix equation, for example, by a CG method (conjugate gradient method), and then performs update of the solution by using the above-mentioned equation (59) (step S2j).

Then, the CPU 1 judges whether the residual of the equation (59) has reached the convergence condition (step S2g). Specifically, the CPU 1 calculates the residual of the equation (59), then compares the result with the convergence condition contained in the calculation condition data D2, and then judges whether the residual of the equation (59) has reached the convergence condition.

Then, when it is judged that the residual has not yet reached the convergence condition, the CPU 1 performs update of the materials property values, and then executes step S2g again. That is, the CPU 1 repeats steps S2f to S2g with performing the update of the materials property values until the residual of the equation (59) reaches the convergence condition.

On the other hand, when it is judged that the residual has reached the convergence condition, the CPU 1 acquires the calculation result (step S2l). Specifically, the CPU 1 stores the solution of the physical value calculated at the immediately preceding step S2i, as the calculation result data into the data storage section 2b so as to achieve the acquisition of the calculation result.

As a result of such solver process (step S2), the flow velocity of air in the cabin space is calculated. Here, such solver process (step S2) corresponds to the calculation method for physical value of the present invention.

When the above-mentioned solver process (step S2) is completed, the CPU 1 executes post process (step S3) on the basis of the post process program P3.

Specifically, for example, in response to an instruction inputted through the GUI, the CPU 1 generates, for example, data of contour of cross section, vector data, equi-contour surface data, and animation data from the calculation result data, and then visualizes the data on the output device 5.

Further, in response to an instruction inputted through the GUI, the CPU 1 extracts quantitative values (a calculation result) in a part of the cabin space and converts them in the form of numerical values or a graph, then visualizes the numerical values and the graph on the output device 5, and further outputs the numerical values and the graph collectively in the form of a file. Further, in response to an instruction inputted through the GUI, on the basis of the calculation result data, the CPU 1 performs, for example, automatic report generation, calculation residual display, and analysis, and then outputs the result.

According to the numerical analysis device A, the numerical analysis method, and the numerical analysis program of the present embodiment, the pre process generates the calculation data model M having the volume of the control volume and the area and the normal vector of the boundary surface, and then the solver process calculates the physical value in each control volume by using the volume of the control volumes and the area and the normal vector of the boundary surface contained in the calculation data model M.

That is, as described in the above-mentioned method for numerical analysis, according to the numerical analysis device A, the numerical analysis method, and the numerical analysis program of the present embodiment, numerical analysis is achieved without generating a calculation data model having Vertex and Connectivity. This also remarkably alleviates restriction on correction or change work for the 3D shape data. Thus, the calculation data model M can be generated far more easily than a calculation data model having Vertex and Connectivity. Thus, work burden is reduced in generation of the calculation data model.

Further, in the numerical analysis device A, the numerical analysis method, and the numerical analysis program according to the present embodiment, in contrast to a conventional method for numerical analysis, the solver process need not calculate the volume of the control volume and the area and the normal vector of the boundary surface by using Vertex and Connectivity. This reduces computation load in the solver process.

Thus, according to the numerical analysis device A, the numerical analysis method, and the numerical analysis program of the present embodiment, work burden is reduced in generation of the calculation data model and computation load is reduced in the solver process.

Further, in the numerical analysis device A, the numerical analysis method, and the numerical analysis program according to the present embodiment, the analysis domain is filled with divided domains without overlapping. Thus, the above-mentioned three conditions (a) to (c) necessary for satisfying the conservation law is satisfied and hence the flow velocity calculation is achieved with satisfying the conservation law.

Here, the calculation data model M according to the present embodiment can be easily generated from mesh data used in a conventional finite volume method or a finite element method, particle data used in a conventional particle method, or simple point group data. Even in this case, correction of divided domains in the boundary area with the outer space is unnecessary in contrast to a voxel method.

For example, in a case that the calculation data model is to be generated from mesh data, each element may be recognized as a divided domain according to the present embodiment (a control volume occupied by a control point) so that the generation is achieved easily. Further, in a case that the calculation data model is to be generated from particle data, a closed space obtained by filling up the analysis domain with closed spaces each surrounding a control point arranged in the analysis domain may be recognized as a divided domain (a control volume occupied by a control point) according to the present embodiment so that the generation is achieved easily.

Further, according to the numerical analysis device A, the numerical analysis method, and the numerical analysis program of the present embodiment, as described above, work burden for the calculation data model in the pre process is reduced remarkably and computation load in the solver process is also reduced.

Figure 24:
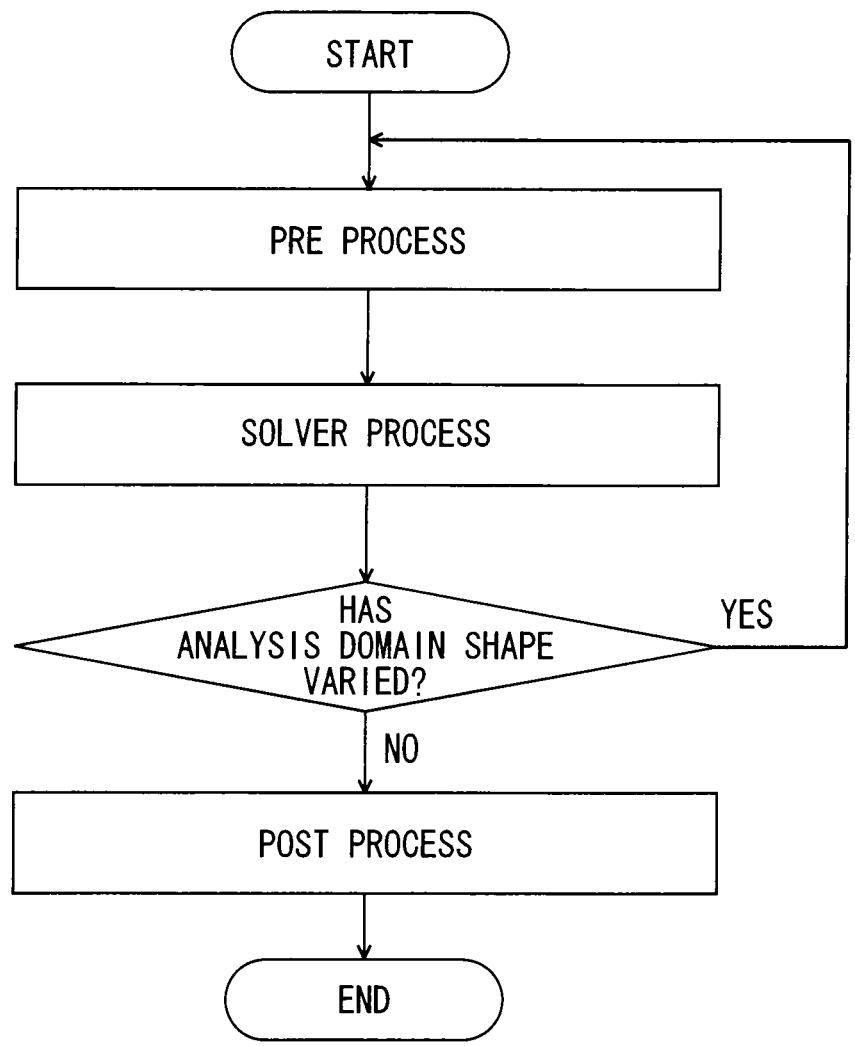
FIG. 24 is a flow chart showing a numerical analysis method in a case that an analysis domain includes a moving boundary, according to an embodiment of the present invention.

Thus, even in a case that the shapes of the analysis domains vary time series, that is, even in a case that the analysis domain includes a moving boundary, the present invention permits physical value calculation within a practical time by repeating the pre process and the solver process at each time that shape change occurs in the analysis domain, as shown in the flow chart of FIG. 24.

Further, in the present embodiment, in the physical value calculation, in a case that the flow velocity on a boundary surface is to be calculated, the weighted average of the flow velocities at the control points located on both sides of the boundary surface calculated by using a weight corresponding to the ratio of the distances from the control points to the boundary surface may be adopted as the flow velocity on the boundary surface.

In such a case, in comparison with a case that the mean of the flow velocities at the control points located on both sides of the boundary surface is simply adopted as the flow velocity on the boundary surface, the flow velocity in the cabin space can be calculated more precisely. Nevertheless, in such a case, the calculation data model need have the data of the ratio E that indicates the internally dividing point where the boundary surface is located on the line segment that joins the control points located on both sides of the boundary surface. For this purpose, the pre process generates the calculation data model M further containing the ratio of the distances from the control points arranged in the inside of adjacent control volumes to the boundary surface located between the control volumes. After that, on the basis of this ratio, the solver process calculates the flow velocity on the boundary surface.

Here, in the physical value calculation, in a case that a vector that joins control points is orthogonal to the boundary surface located between the control points, the physical value calculation may be performed with replacing the normal vector with the unit vector of the distance vector that joins the control points.

Nevertheless, in such a case, the calculation data mode need have data indicating the above-mentioned distance vector or alternatively the position coordinates of the control points necessary for calculating the distance vector. Thus, the pre process generates the calculation data model M that further includes the distance vector joining individual control points arranged in the inside of adjacent control volumes or alternatively coordinates of the control points necessary for calculating the distance vector. Then, when the distance vector is orthogonal to the boundary surface between the control points, the flow velocity is calculated with replacing the distance vector with the normal vector of the boundary surface.

A preferred embodiment of the present invention has been described above with reference to the accompanying drawings. However, obviously, the present invention is not limited to the above-mentioned embodiment. The shapes, the combinations, and the like of the component members shown in the embodiment are examples and may be changed variously in accordance with a design requirement or the like within a range not departing from the spirit of the present invention.

The above-mentioned embodiment has been described for a configuration that the flow velocity of air is calculated by numerical analysis by using discretized governing equations derived from the Navier-Stokes equations which is a modification of the equation for conservation of momentum and from the continuity equation.

However, the present invention is not limited to this. That is, physical values may be calculated by numerical analysis by using a discretized governing equation derived from at least any one of the mass conservation equation, the equation for conservation of momentum, the equation of conservation of angular momentum, the equation for conservation of energy, the advection diffusion equation, and the wave equation.

Further, the above-mentioned embodiment has been described for a configuration that the normal vector of the boundary surface and the area of the boundary surface are employed as the characteristic value of boundary surface according to the present invention.

However, the present invention is not limited to this. That is, another quantity (i.e., the contour length of the boundary surface) may be employed as a characteristic value of boundary surface.

Further, the above-mentioned embodiment has been described for a configuration that the calculation data model is generated such that the above-mentioned three conditions necessary for satisfying the conservation law are satisfied.

However, the present invention is not limited to this. That is, in a case that the conservation law need not be satisfied, the calculation data model need not be generated such that the above-mentioned three conditions are satisfied.

Further, the above-mentioned embodiment has been described for a configuration that the volume of a divided domain is recognized as the volume of the control volume occupied by the control point arranged inside the divided domain.

However, the present invention is not limited to this. That is, the control point need not be arranged in the inside of the divided domain. In such a case, the numerical analysis is achieved with replacing the volume of the control volume occupied by a control point with the volume of the divided domain.

Further, the above-mentioned embodiment has been described for a configuration that the numerical analysis program P is portable in a state of being stored in the DVD medium X.

However, the present invention is not limited to this. That is, a configuration may be employed that the numerical analysis program P is portable in a state of being stored in another removable medium.

Further, the pre process program P1 and the solver process program P2 may be stored in mutually separate removable media in a portable manner. Further, the numerical analysis program P may be transmitted through a network.

Further, the above-mentioned embodiment has been described for a configuration that each boundary surface is a plane. However, the present invention is not limited to this. That is, any boundary surface may be a curved surface.

The present application has been described in detail with reference to a particular embodiment. However, it is obvious to the person skilled in the art that various kinds of alterations and corrections may be performed without departing from the spirit and the scope of the present invention.

The present application is based on the Japanese Patent Application (Japanese Laid-Open Patent Application No. 2009-150945) filed on Jun. 25, 2009. The contents are incorporated herein by reference.

DESCRIPTION OF REFERENCE NUMERALS

A ... numerical analysis device (calculation device for physical value)
P ... numerical analysis program
P1 ... pre process program
P2 ... solver process program (calculation program for physical value)
P3 ... post process program
M ... calculation data model
$V_i$ ... volume virtually occupied by particle i
$S_{ij}$ ... boundary surface area between particle i and particle j
$r_{ij}$ ... distance vector from i to j
$n_{ij}$ ... normal vector of $S_{ij}$
1 ... CPU
2 ... memory device
2a ... memory device for programs
2b ... data storage section
3 ... DVD drive
4 ... input device
4a ... keyboard
4b ... mouse
5 ... output device
5a ... display
5b ... printer

The invention claimed is:

1. A calculation method for physical value by a computer, for calculating physical values in a numerical analysis method for numerically analyzing a physical phenomenon, comprising:
  calculating, by the computer, physical values in an analysis domain divided into a plurality of divided domains, wherein the computer calculates the physical values by:
    reading, from a memory, a discretized governing equation that uses only values not requiring coordinates of vertices of the divided domains and connectivity information of the vertices and that is derived on the basis of a weighted residual method; and
    using a calculation data model in which volumes of the divided domains and characteristic values of boundary surface indicating characteristics of boundary surfaces of adjacent ones of the divided domains are provided as the values not requiring coordinates of vertices of the divided domains and connectivity information of the vertices, and the governing equation.

2. The calculation method for physical value according to claim 1, wherein
  the discretized governing equation is preliminarily derived from a mass conservation equation, an equation for conservation of momentum, an equation for conservation of energy, an advection diffusion equation, and a wave equation, and
  the governing equation is stored in the memory.

3. The calculation method for physical value according to claim 1, wherein
  the characteristic values of boundary surface are areas of the boundary surfaces and normal vectors of the boundary surfaces.

4. A numerical analysis method, comprising:
a pre process for generating a calculation data model by the computer; and
a solver process for calculating physical values in the analysis domain by a calculation method for physical value based on the calculation data model and the governing equation, wherein
in the solver process, the computer uses the calculation method for physical value according to claim 1.

5. The numerical analysis method according to claim 4, wherein the computer forms the divided domains such that
in the pre process, a condition that a total sum of volumes of all divided domains agrees with the volume of the analysis domain, a condition that areas of the boundary surfaces agree with each other, a condition that the absolute values of the normal vectors agree with each other between that viewed from one of divided domains facing the boundary surface and that viewed from the other of the divided domains, and a condition that the following equation holds when a unit normal vector in an arbitrary direction of an infinitely large projection plane P passing through the divided domain is $[n]_P$, an area of the boundary surface is $S_i$, a unit normal vector of the boundary surface is $[n]_i$, a total number of surfaces of the divided domain is m, and each character surrounded by the above-mentioned [ ] is a bold font denoting a vector are satisfied:

$$\sum_{i=1}^{m} [(n_i \cdot n_P) \cdot S_i] = 0.$$

6. The numerical analysis method according to claim 5, wherein
the computer satisfies the conditions by filling the analysis domain with the divided domains without overlapping.

7. The numerical analysis method according to claim 4, wherein
the computer generates the calculation data model further including a ratio of distances from control points arranged in the inside of adjacent ones of the divided domains to the boundary surface faced by the divided domains in the pre process, and the computer calculates physical values on the boundary surface using the ratio in the solver process.

8. The numerical analysis method according to claim 4, wherein
the computer generates the calculation data model that further includes distance vectors joining individual control points arranged in the inside of adjacent ones of the divided domains or alternatively coordinates of the control points for calculating the distance vectors in the pre process, and when the distance vector is orthogonal to the boundary surface between the control points, the computer calculates the physical values by adopting the distance vector as one of the characteristic values of boundary surface in the solver process.

9. The numerical analysis method according to claim 4, wherein
in a case that the analysis domain includes a moving boundary, the computer performs the pre process and the solver process at each time that the moving boundary moves.

10. The calculation method of claim 1, further comprising:
obtaining the discretized governing equation by stopping, in a middle, a process of deriving, using the weighted residual method, an equation using values that set forth a geometric shape.

11. A non-transitory computer-readable medium storing a calculation program for physical value for causing a computer to execute a calculation method for physical value, for calculating physical values in a numerical analysis method for numerically analyzing a physical phenomenon, the calculation method for physical value comprising:
calculating physical values in an analysis domain divided into a plurality of divided domains, wherein the physical values are calculated by using:
a discretized governing equation that uses only values not requiring coordinates of vertices of the divided domains and connectivity information of the vertices and that is derived on the basis of a weighted residual method; and
a calculation data model in which volumes of the divided domains and characteristic values of boundary surface indicating characteristics of boundary surfaces of adjacent ones of the divided domains are provided as the values not requiring coordinates of vertices of the divided domains and connectivity information of the vertices.

12. The non-transitory computer-readable medium according to claim 11, wherein
the discretized governing equation is derived from a mass conservation equation, an equation for conservation of momentum, an equation for conservation of energy, an advection diffusion equation, and a wave equation.

13. The non-transitory computer-readable medium according to claim 11, wherein
the characteristic value of boundary surface are areas of the boundary surfaces and normal vectors of the boundary surfaces.

14. A non-transitory computer-readable medium storing a numerical analysis program for causing a computer to execute a numerical analysis method comprising:
a pre process for generating a calculation data model; and
a solver process for calculating physical values in the analysis domain by a calculation method for physical value based on the calculation data model and the governing equation,
wherein in the solver process, the calculation program for physical value according to claim 11 is used.

15. The non-transitory computer-readable medium according to claim 14, wherein the divided domains are formed such that
in the pre process, a condition that a total sum of volumes of all divided domains agrees with the volume of the analysis domain, a condition that areas of the boundary surfaces agree with each other, a condition that the absolute values of the normal vectors agree with each other between that viewed from one of divided domains facing the boundary surface and that viewed from the other of the divided domains, and a condition that the following equation holds when a unit normal vector in an arbitrary direction of an infinitely large projection plane P passing through the divided domain is $[n]_P$, an area of the boundary surface is $S_i$, a unit normal vector of the boundary surface is $[n]_i$, a total number of surfaces of the divided domain is m, and each character surrounded by the above-mentioned [ ] is a bold font denoting a vector are satisfied:

$$\sum_{i=1}^{m}[(n_i \cdot n_P) \cdot S_i] = 0.$$

16. The non-transitory computer-readable medium according claim 15, wherein
the conditions are satisfied by filling the analysis domain with the divided domains without overlapping.

17. The non-transitory computer-readable medium according to claim 14, wherein
the pre process generates the calculation data model further including a ratio of distances from control points arranged in the inside of adjacent ones of the divided domains to the boundary surface faced by the divided domains and the solver process calculates physical values on the boundary surface using the ratio.

18. The non-transitory computer-readable medium according to claim 14, wherein
the pre process generates the calculation data model that further includes distance vectors joining individual control points arranged in the inside of adjacent ones of the divided domains or alternatively coordinates of the control points for calculating the distance vectors, and when the distance vector is orthogonal to boundary surface between the control points, the physical values are calculated by adopting the distance vector as one of the characteristic values of boundary surface.

19. The non-transitory computer-readable medium according to claim 14, wherein
in a case that the analysis domain includes a moving boundary, the pre process and the solver process are performed at each time that the moving boundary moves.

20. The non-transitory computer-readable medium of claim 11, further comprising:
obtaining the discretized governing equation by stopping, in a middle, a process of deriving, using the weighted residual method, an equation using values that set forth a geometric shape.

21. A calculation device for physical value that performs the calculation method for physical value, for calculating physical values in a numerical analysis method for numerically analyzing a physical phenomenon, comprising:
a calculation unit configured to calculate physical values in an analysis domain divided into a plurality of divided domains; and
a memory configured to store the physical values that are calculated by using a discretized governing equation that uses only values not requiring coordinates of vertices of the divided domains and connectivity information of the vertices and that is derived on the basis of a weighted residual method, wherein
the calculation unit is configured to calculate the physical values by using a calculation data model in which volumes of the divided domains and characteristic values of boundary surface indicating characteristics of boundary surfaces of adjacent ones of the divided domains are provided as the values not requiring coordinates of vertices of the divided domains and connectivity information of the vertices, and the governing equation.

22. The calculation device for physical value according to claim 21, wherein
the discretized governing equation is preliminarily derived from a mass conservation equation, an equation for conservation of momentum, an equation for conservation of energy, an advection diffusion equation, and a wave equation, and
the governing equation is stored in the memory.

23. The calculation device for physical value according to claim 21, wherein
the characteristic values of boundary surface are areas of the boundary surfaces and normal vectors of the boundary surfaces.

24. A numerical analysis device that performs the numerical analysis method comprising:
a calculation data model generating unit configured to perform a pre process for generating a calculation data model; and
a calculation unit for physical value comprising the calculation device for physical value according to claim 21, the calculation unit for physical value performing a solver process for calculating physical values in the analysis domain by calculation of the calculation device based on the calculation data model and the governing equation.

25. The numerical analysis device according to claim 24, wherein the calculation data model generating unit is configured to form the divided domains such that
a condition that a total sum of volumes of all divided domains agrees with the volume of the analysis domain, a condition that areas of the boundary surfaces agree with each other, a condition that the absolute values of the normal vectors agree with each other between that viewed from one of divided domains facing the boundary surface and that viewed from the other of the divided domains, and a condition that the following equation holds when a unit normal vector in an arbitrary direction of an infinitely large projection plane P passing through the divided domain is $[n]_p$, an area of the boundary surface is $S_i$, a unit normal vector of the boundary surface is $[n]_i$, a total number of surfaces of the divided domain is m, and each character surrounded by the above-mentioned [ ] is a bold font denoting a vector are satisfied:

$$\sum_{i=1}^{m}[(n_i \cdot n_P) \cdot S_i] = 0.$$

26. The numerical analysis device according to claim 25, wherein
the calculation data model generating unit is configured to satisfy the conditions by filling the analysis domain with the divided domains without overlapping.

27. The numerical analysis device according to claim 24, wherein:
the calculation data model generating unit is configured to generate the calculation data model further including a ratio of distances from control points arranged in the inside of adjacent ones of the divided domains to the boundary surface faced by the divided domains in the pre process; and
the calculation unit for physical value is configured to calculate physical values on the boundary surface using the ratio in the solver process.

28. The numerical analysis device according to claim 24, wherein:
the calculation data model generating unit is configured to generate the calculation data model that further includes distance vectors joining individual control points arranged in the inside of adjacent ones of the divided domains or alternatively coordinates of the control points for calculating the distance vectors; and when the distance vector is orthogonal to the boundary surface between the control points, the calculation unit for physical value calculates the physical values by adopting the distance vector as one of the characteristic values of boundary surface in the solver process.

29. The numerical analysis device according to claim 24, wherein in a case that the analysis domain includes a moving boundary, the calculation data model generating unit and the calculation unit for physical value perform the pre process and the solver process at each time that the moving boundary moves.

30. The calculation device of claim 21, wherein the calculation unit is configured to obtain the discretized governing equation by stopping, in a middle, a process of deriving, using the weighted residual method, an equation using values that set forth a geometric shape.

* * * * *